(12) United States Patent
Buchwald et al.

(10) Patent No.: US 7,309,799 B2
(45) Date of Patent: Dec. 18, 2007

(54) METHODS FOR THE SYNTHESIS OF MILNACIPRAN AND CONGENERS THEREOF

(75) Inventors: Stephen L. Buchwald, Newton, MA (US); Timothy M. Swager, Newton, MA (US); Roman V. Rariy, Allston, MA (US)

(73) Assignee: Collegium Pharmaceutical, Inc., Cumberland, RI (US)

( * ) Notice: Subject to any disclaimer, the term of this patent is extended or adjusted under 35 U.S.C. 154(b) by 175 days.

(21) Appl. No.: 11/097,466

(22) Filed: Apr. 1, 2005

(65) Prior Publication Data

US 2005/0282898 A1    Dec. 22, 2005

Related U.S. Application Data

(60) Provisional application No. 60/576,010, filed on Jun. 1, 2004.

(51) Int. Cl.
  *C07C 211/00* (2006.01)
  *C07C 231/00* (2006.01)
(52) U.S. Cl. .................... 564/133; 564/461
(58) Field of Classification Search ............ 562/506; 564/123, 164, 165, 190; 548/473, 480, 477
  See application file for complete search history.

(56) References Cited

OTHER PUBLICATIONS

Casadio et al., Bollettino Chimico Farmaceutico (1978), 117(6), 331-42, CAS online citation on STN, Columbus OH, USA.*
Wang et al., Zhongguo Yiyao Gongye Zazhi (2004), 35(5), 259-260, CAS online citation on STN, Columbus OH, USA.*
Bonnaud, B, et al., "1-Aryl-2-(aminoethyl)cyclopropanecarboxylic Acid Derivatives. A New Series of Potential Antidepressants", *J. Med. Chem.*, 30:318-325 (1987).
Bonnaud, B., et al., "Synthesis of Novel Indolizine Derivatives", *J. Heterocyclic Chem.*, 28:1927-1932 (1991).
Ronsisvalle, G. et al., "Substituted 1-Phenyl-2-cyclopropylmethylamines with High Affinity and Selectivity for Sigma Sites", *Bioorg. & Med. Chem.*, 8:1503-1513 (2000).
Shuto, S. et al., "Synthesis of (+)- and (−)-Milnaciprans and Their Conformationally Restricted Analogs", *Tetrahedron Letters*, 37(5):641-644 (1996).
Partial International Search Report issued for corresponding PCT application No. PCT/US2005/011365.
International Search Report issued for corresponding PCT application No. PCT/US2005/011365 dated Feb. 2, 2006.

* cited by examiner

*Primary Examiner*—Karl Puttlitz
(74) *Attorney, Agent, or Firm*—Foley Hoag LLP; Dana M. Gordon

(57) ABSTRACT

One aspect of the present invention relates to methods for synthesizing milnacipran or congeners thereof. Another aspect of the present invention relates to asymmetric methods for synthesizing enantiomerically enriched milnacipran or congeners thereof. The present invention also relates to methods for synthesizing intermediates useful in the non-asymmetric or asymmetric methods for synthesizing enantiomerically enriched milnacipran or congeners thereof.

6 Claims, 15 Drawing Sheets

*Milnacipran*

*Milnacipran Congeners*

*May be enantiomerically enriched*

METHODS FOR THE SYNTHESIS OF MILNACIPRAN AND CONGENERS THEREOF

RELATED APPLICATIONS

This application claims the benefit of priority to U.S. Provisional Patent Application Ser. No. 60/576,010, filed Jun. 1, 2004; the contents of which is incorporated by reference.

BACKGROUND OF THE INVENTION

Early antidepressant medications, e.g., tricyclic antidepressants (TCAs) and monoamine oxidase inhibitors (MAOIs), are effective because they enhance either noradrenergic or serotonergic mechanisms or both. Unfortunately, these compounds block cholinergic, histaminergic and alpha-1-adrenergic receptor sites, interact with a number of other medications and bring about numerous undesirable side effects. Several chemically unrelated agents have been developed and introduced in the past decade to supplement the early antidepressants. These include selective inhibitors of the reuptake of serotonin (the selective serotonin reuptake inhibitors (SSRIs)) or noradrenaline (reboxetine) or both (SNRIs: milnacipran and venlafaxine), as well as drugs with distinct neurochemical profiles, such as mirtazapine, nefazodone, moclobemide and tianeptine.

Milnacipran (racemic cis-2-(aminomethyl)-N,N-diethyl-1-phenyl-cyclopropanecarboxamide) is a well-characterized small molecule that functions through several mechanisms, including re-uptake inhibition of serotonin and noradrenaline. This agent was discovered and originally developed for treatment of major depressive disorders ("MDD"). See, e.g., U.S. Pat. No. 4,478,836. Clinical development was initiated in the late 1980s, and a large number of toxicology, pharmacology, mechanism and safety trials were conducted at that time. Through the mid-1990s numerous human clinical trials were conducted, leading to approvals for MDD in France and over 20 other countries beginning in 1997.

The safety and efficacy of milnacipran for treatment of MDD have been extensively documented throughout this process. In addition, milnacipran has been evaluated on a more limited basis for the treatment of anxiety and chronic pain. Milnacipran has an excellent safety profile, backed by an extensive database consisting of over 400,000 patient-exposures during more than 4 years of commercial marketing. Safety has been characterized in male and female adults, ranging in age from 18 to over 80, and in patients with various concomitant illnesses. Moreover, relatively few contraindications have been discovered.

Milnacipran inhibits with essentially equal potency the reuptake of serotonin and noradrenaline, with no detectable affinity for any neurotransmitter receptor studied. See generally Puech, A. et al. *Int. Clin. Psychopharmacol.* 1997, 12, 99-108. A review of the studies comparing milnacipran, placebo and active comparator antidepressants provides clear-cut evidence of its efficacy in both severe and moderate depression in hospitalized and community settings. Meta-analyses of the original data of controlled trials involving 1032 patients, comparing milnacipran with imipramine or selective serotonin reuptake inhibitors (SSRIs), show that milnacipran provides antidepressant efficacy similar to that of imipramine and significantly superior to that of the SSRIs. An analysis of a database of over 3300 patients shows that both the general and cardiovascular tolerability of milnacipran are superior to those of the tricyclic antidepressants (TCAs) with fewer cholinergic side-effects. The tolerability of milnacipran was comparable to that of the SSRIs, with a higher incidence of dysuria with milnacipran, and a higher frequency of nausea and anxiety with the SSRIs. Therefore, milnacipran is a therapeutic option in depression, offering a clinical efficacy in the range of the TCAs combined with a tolerability equivalent to that of the SSRIs.

Antidepressants of all types represent a common form of therapy for a variety of chronic pain conditions, and studies have demonstrated that the analgesic effects of these drugs are independent of their influence on mood. Agents that interfere with the reuptake of norepinephrine, particularly tricyclic antidepressants (TCAs), have demonstrated superior analgesic efficacy compared to agents that selectively block the reuptake of serotonin. Unfortunately, many patients are unable to tolerate the side effects associated with TCAs. Thus, there has been an effort to find agents that affect norepinephrine reuptake, but improve upon the side effect profile of TCAs.

Milnacipran and duloxetine have been compared in an experimental nerve injury model known as spinal nerve ligation (SNL). SNL induces behavioral signs in rats that are similar to human states of neuropathic pain, including increased sensitivity to light touch (mechanical hypersensitivity) and increased sensitivity to heat (thermal hypersensitivity). The results of the study indicated that milnacipran and duloxetine both reversed SNL-induced thermal hypersensitivity, but that milnacipran was more effective in reversing the SNL induced thermal hypersensitivity than duloxetine. This finding was consistent with other studies indicating that drugs that interfere with norepinephrine reuptake, compared to drugs that interfere more with serotonin reuptake, have superior analgesic properties. Neither milnacipran nor duloxetine reversed mechanical hypersensitivity, consistent with the profile of amitriptyline, a TCA, in this model.

Despite its acceptance as a highly desirable drug for the treatment of depression and other disorders, including fibromyalgia, there are side effects associated with the use of milnacipran. There are also occasional issues with patient compliance. Although milnacipran is effective in treating major depressive episodes, more suitable methods are needed. These methods include, e.g., administering more efficacious amounts of milnacipran, i.e., above 100 mg daily dosages of milnacipran. These daily dosages would preferably result in an improved efficacy of the milnacipran, the maintenance of excellent patient tolerability, the maintenance of a positive patient safety profile (e.g., dose limiting toxicity), a suitable peak plasma concentration ($C_{max}$) of milnacipran, and/or a once-a-day (QD), as opposed to twice-a-day (BID).

Adverse reactions to the oral administration of milnacipran include at least one of the following: nausea, vomiting, headache, tremulousness, anxiety, panic attack, palpitations, urinary retention, orthostatic hypotension, diaphoresis, chest pain, rash, weight increase, back pain, constipation, vertigo, increased sweating, agitation, hot flushes, tremors, fatigue, somnolence, dyspepsia, dysoria, nervousness, dry mouth, abdominal pain, irritability, and insomnia. One frequently mentioned dose-limiting side effect of Milnacipran was gastrointestinal disturbances, including nausea and vomiting with increasing frequency after doses of 100 mg or above. The highest incidence of nausea and vomiting was observed in a pharmacokinetic study in which subjects fasted prior to study drug administration. Clinical trials in which study drug was administered at meal time showed significantly improved gastrointestinal tolerability. These data indicate that local Milnacipran effects (direct influence on the stomach surface) are quite substantial. No information is available regarding local effects of pure enantiomers of milnacipran. In addition, a direct irritant effect of milnacipran on gastric mucosa was found in preclinical studies. The incidence of certain adverse events increases with dosage, including nausea, vomiting, sweating, hot flushes, palpitations, tremor, anxiety, dysuria, and sleep disturbances.

The (+)-dextro enantiomer of milnacipran (F2695, (+)-1S,2R-milnacipran) is roughly twice as active in inhibiting norepinephrine and serotonin reuptake as the racemic mixture. See Viazzo et al. *Tetrahedron Lett.* 1996, 37, 4519-4522; Deprez et al. *Eur. J. Drug Metab. Pharmacokinet.* 1998, 23, 166-171. Moreover, the (−)-levro enantiomer of milnacipran (F2696, (−)-1R,2S-milnacipran) is much less potent. See id.

SUMMARY OF THE INVENTION

One aspect of the present invention relates to methods for synthesizing milnacipran or congeners thereof. Another aspect of the present invention relates to asymmetric methods for synthesizing enantiomerically enriched milnacipran or congeners thereof. The present invention also relates to methods for synthesizing intermediates useful in the non-asymmetric or asymmetric methods for synthesizing enantiomerically enriched milnacipran or congeners thereof.

DETAILED DESCRIPTION OF THE INVENTION

Overview

Figure 1:
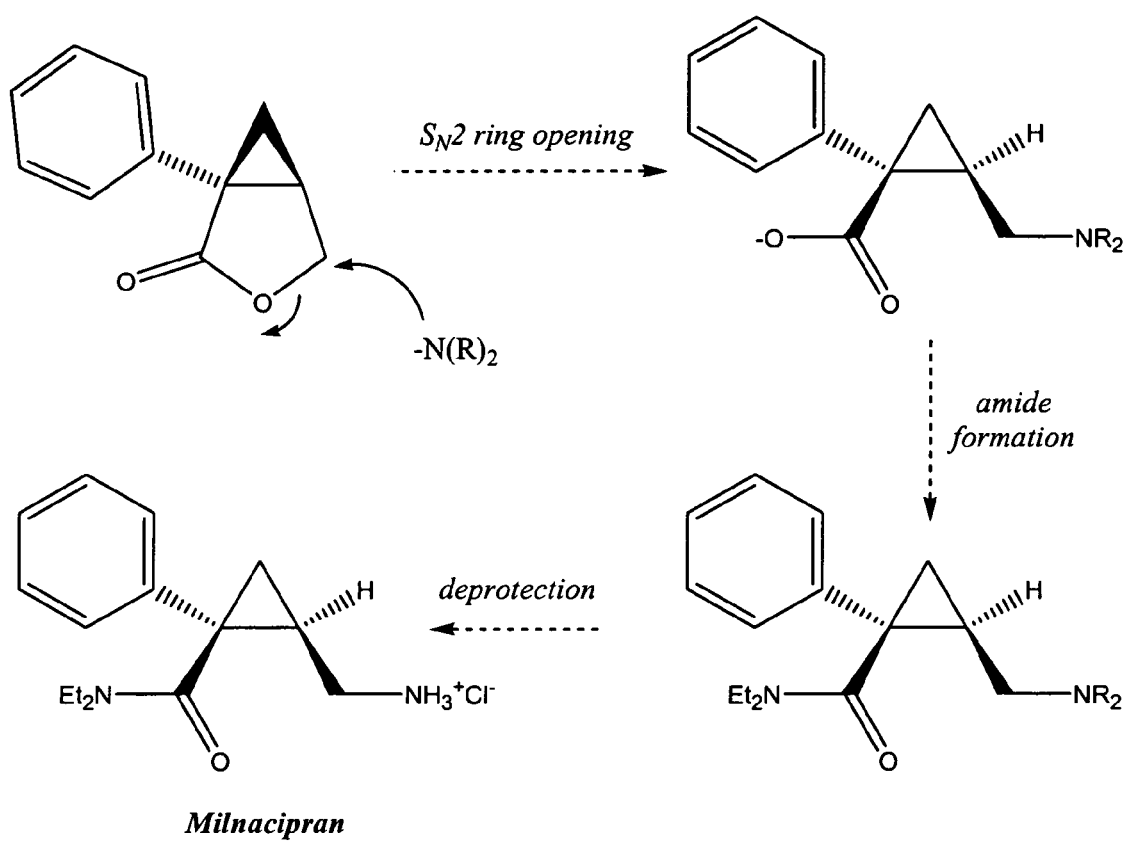
FIG. 1 depicts a preferred combination of the methods of the present invention, which taken together constitutes a scheme for the synthesis of milnacipran.
Figure 2:
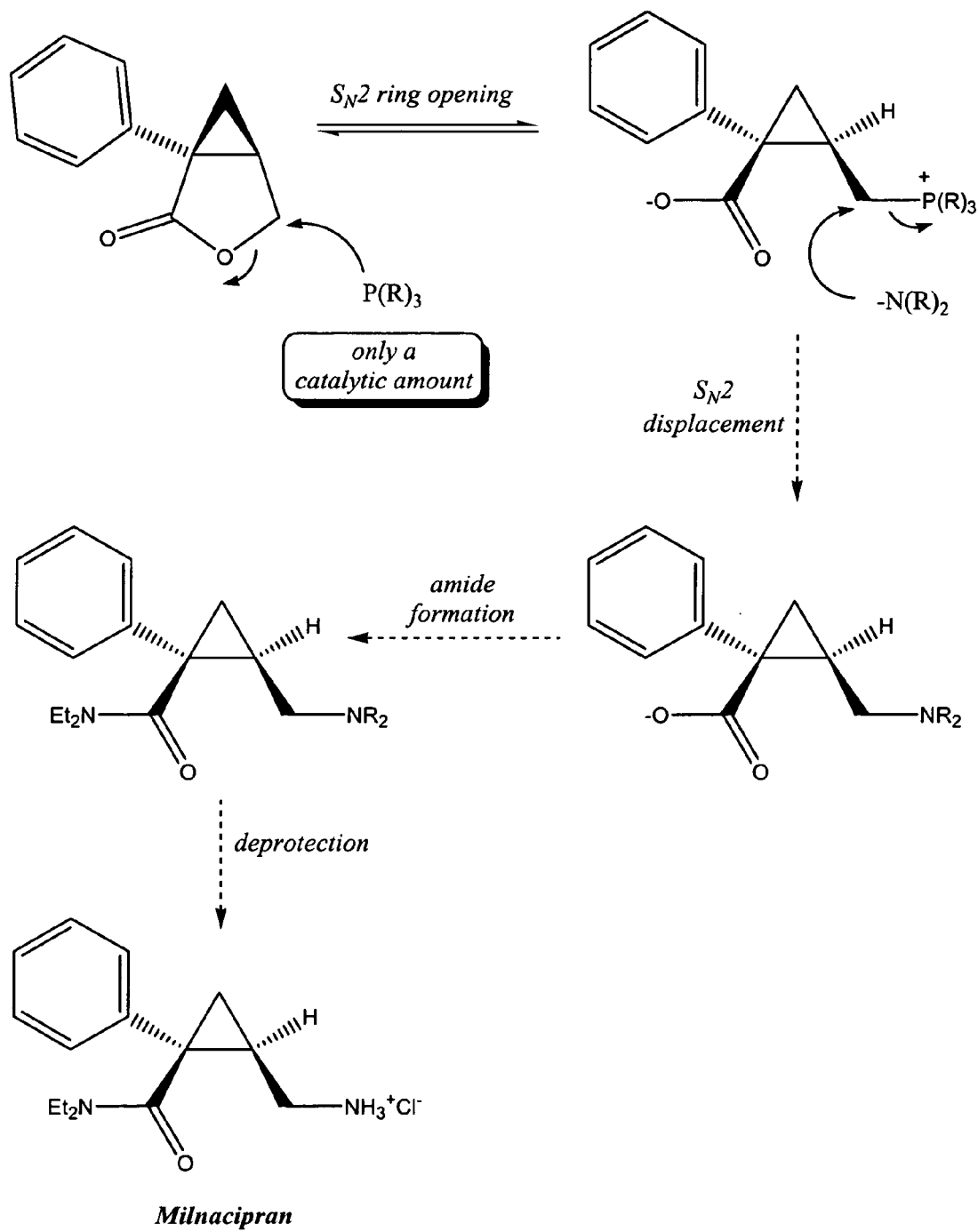
FIG. 2 depicts a preferred combination of the methods of the present invention, which taken together constitutes a scheme for the synthesis of milnacipran.
Figure 3:
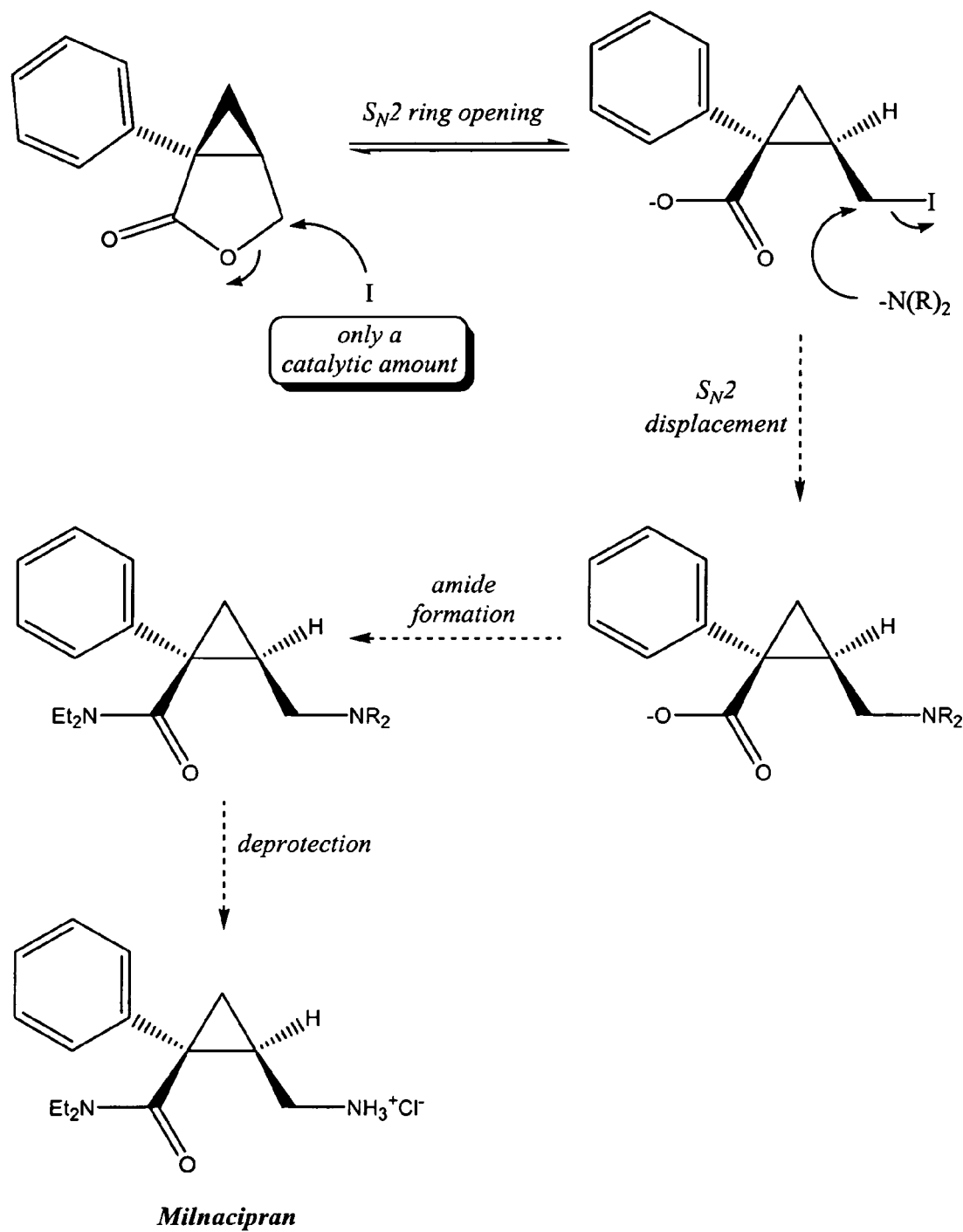
FIG. 3 depicts a preferred combination of the methods of the present invention, which taken together constitutes a scheme for the synthesis of milnacipran.
Figure 4:
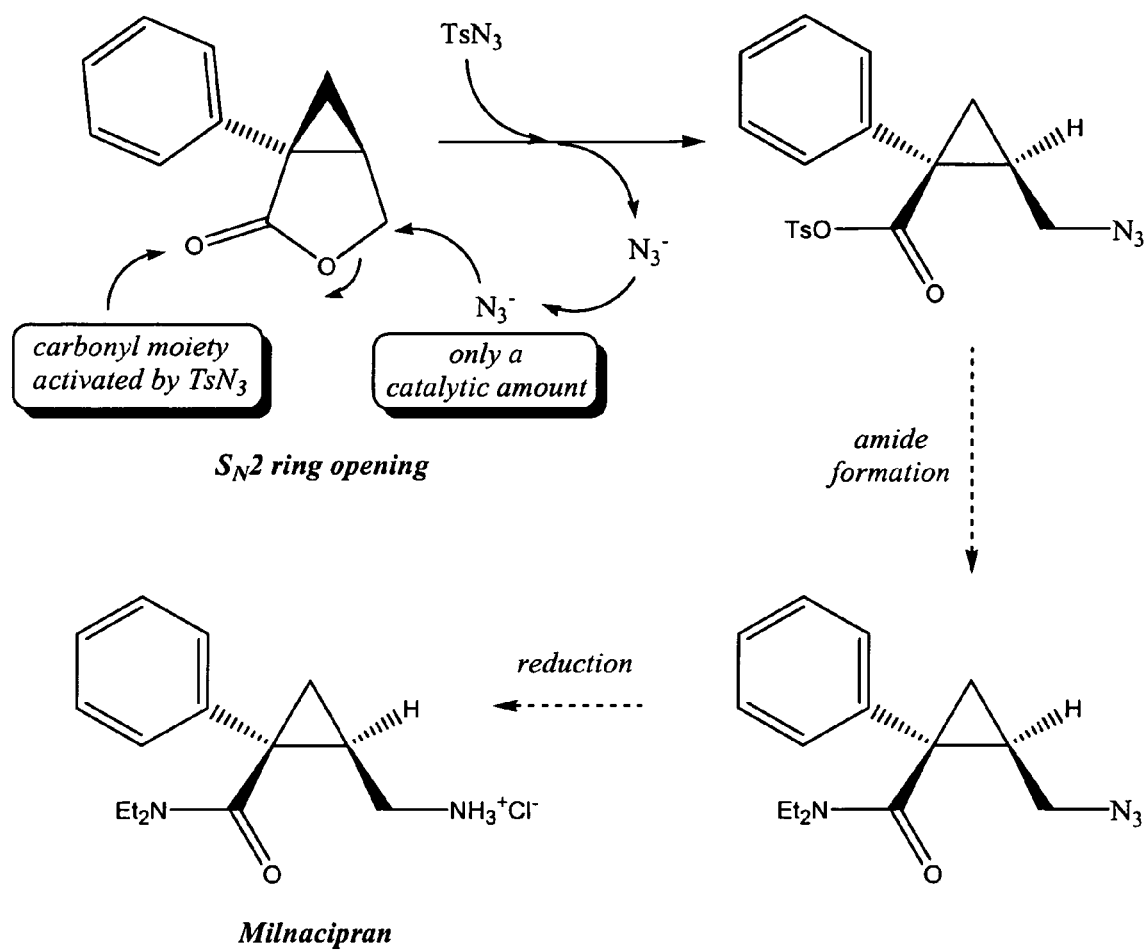
FIG. 4 depicts a preferred combination of the methods of the present invention, which taken together constitutes a scheme for the synthesis of milnacipran.
Figure 5:
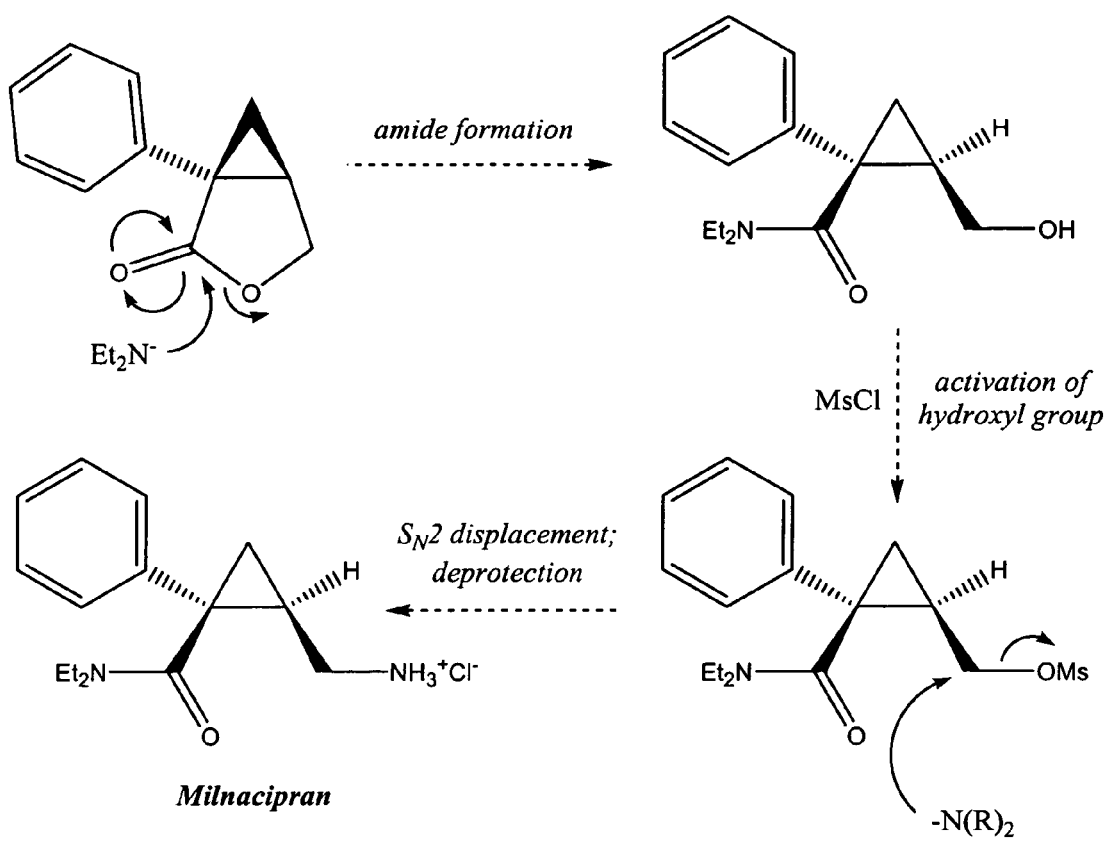
FIG. 5 depicts a preferred combination of the methods of the present invention, which taken together constitutes a scheme for the synthesis of milnacipran.
Figure 6:
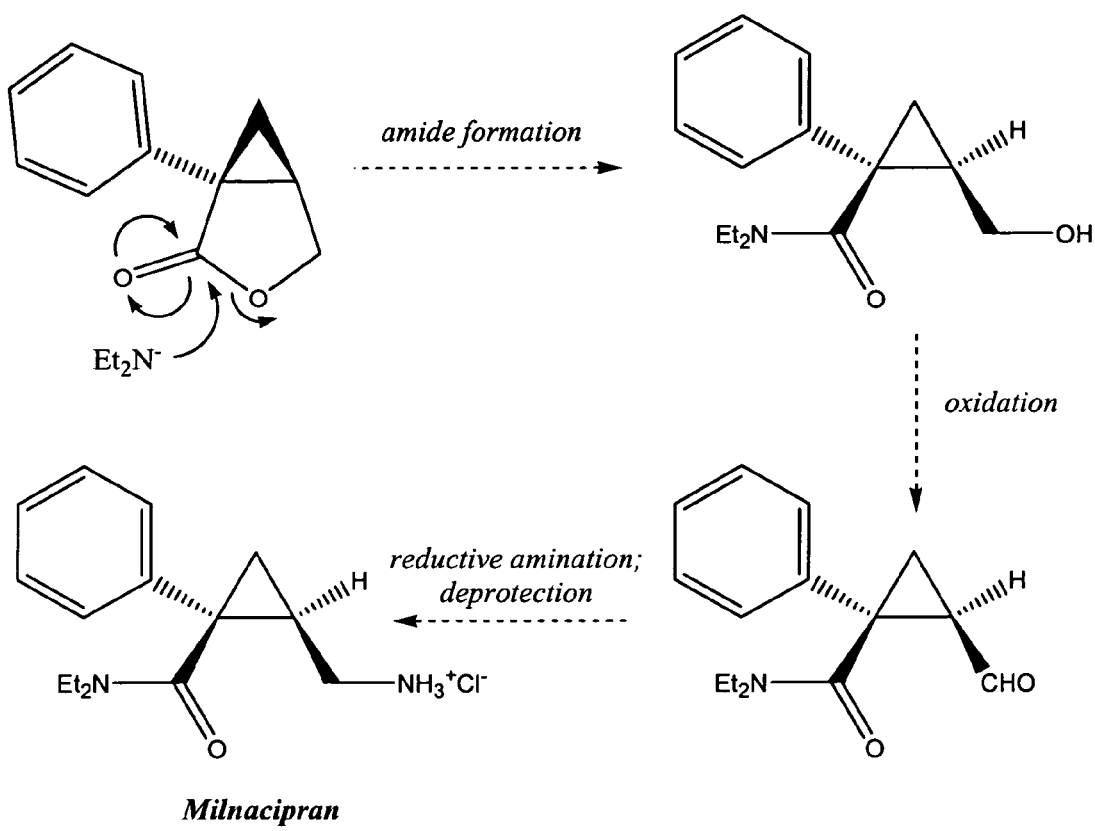
FIG. 6 depicts a preferred combination of the methods of the present invention, which taken together constitutes a scheme for the synthesis of milnacipran.
Figure 7:
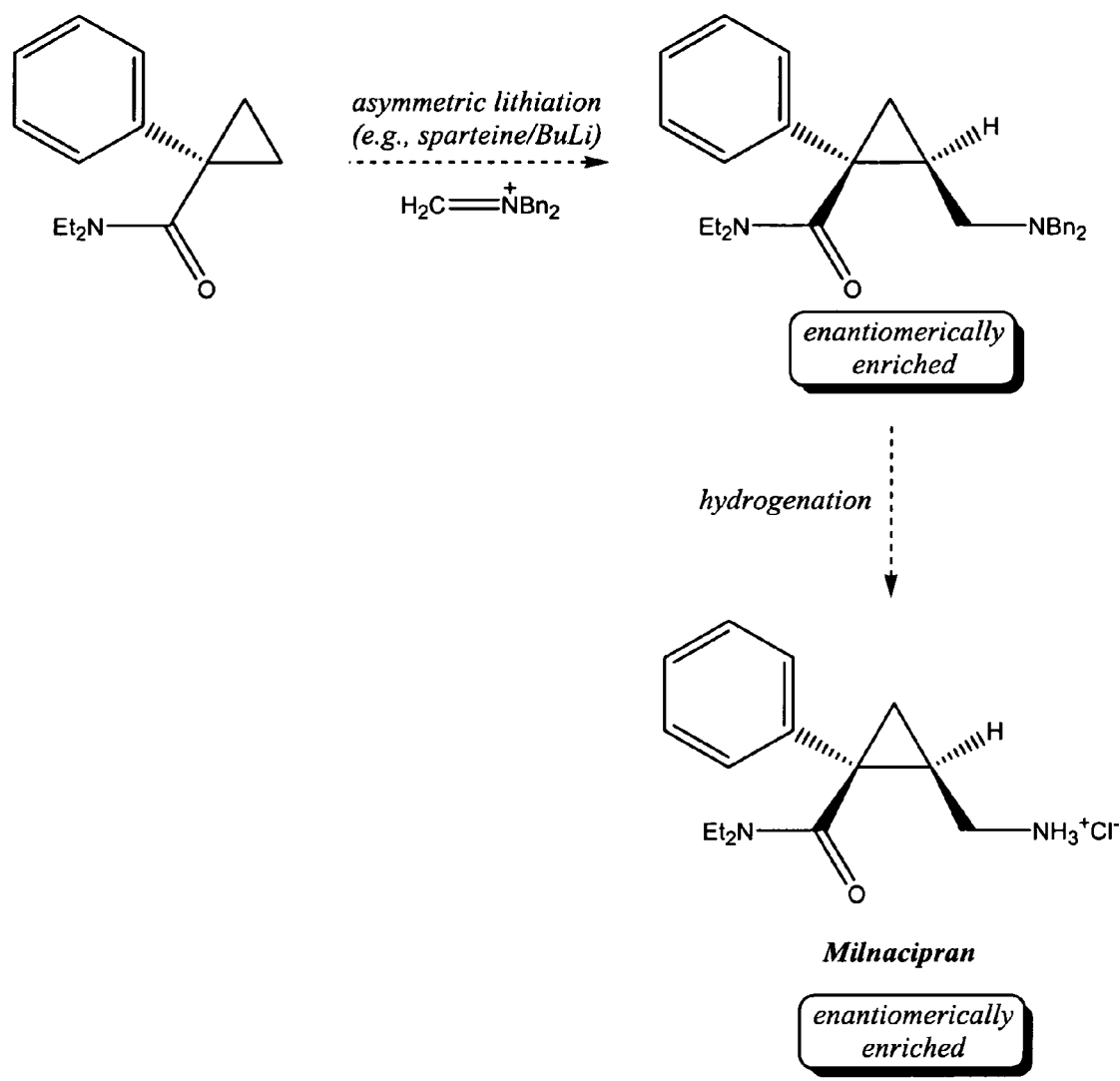
FIG. 7 depicts a preferred combination of the methods of the present invention, which taken together constitutes a scheme for the asymmetric synthesis of milnacipran.
Figure 8:
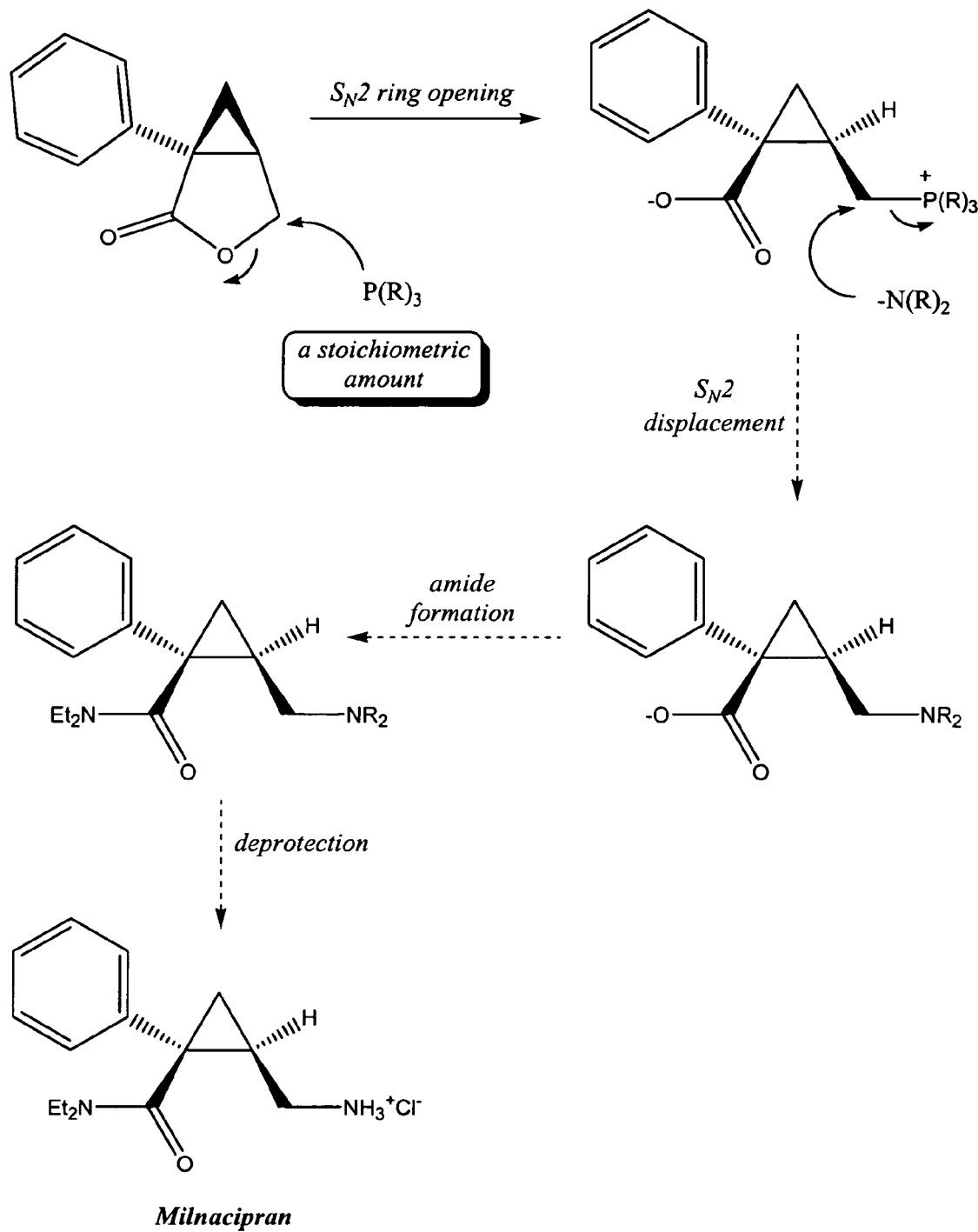
FIG. 8 depicts a preferred combination of the methods of the present invention, which taken together constitutes a scheme for the synthesis of milnacipran.
Figure 9:
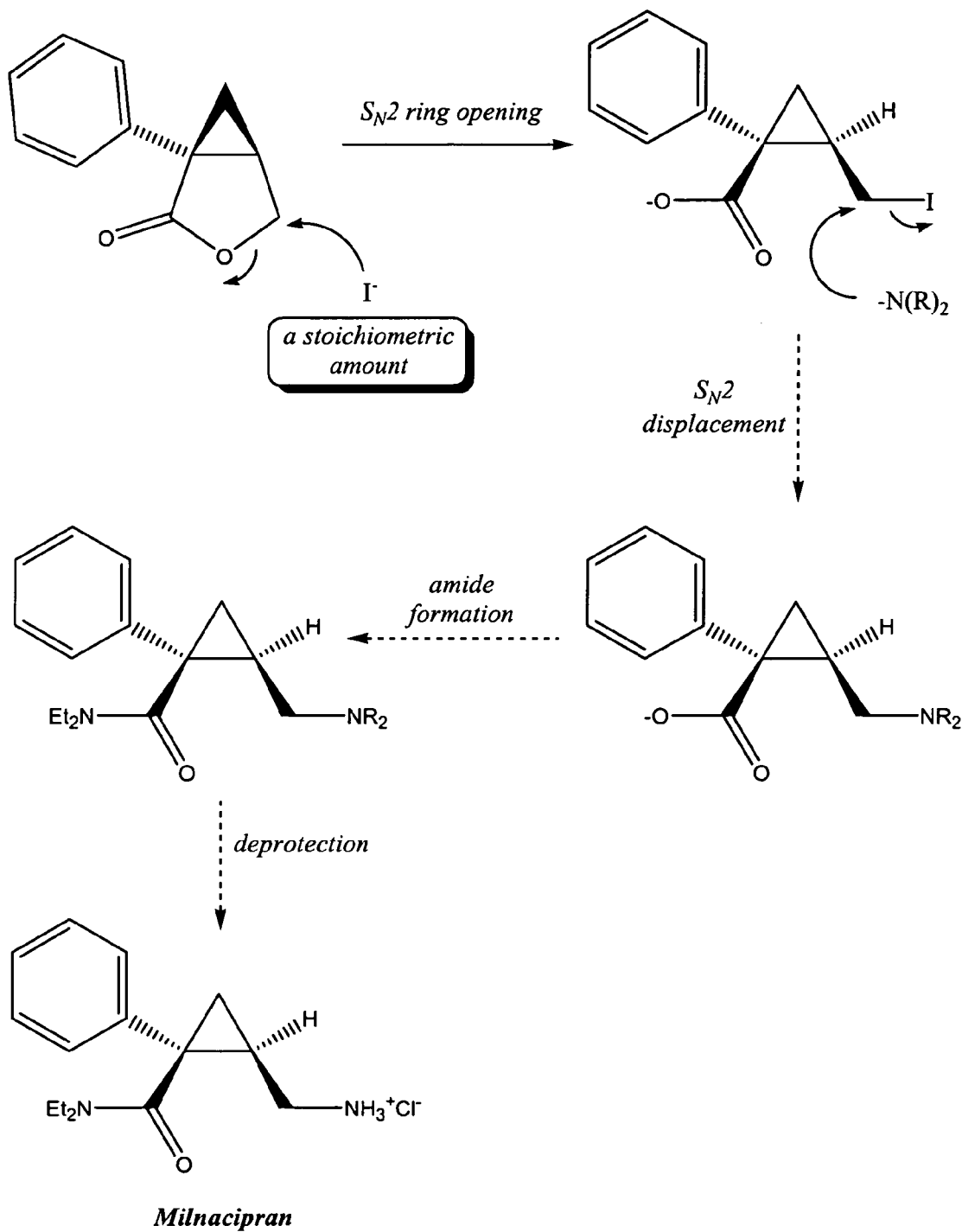
FIG. 9 depicts a preferred combination of the methods of the present invention, which taken together constitutes a scheme for the synthesis of milnacipran.
Figure 10:
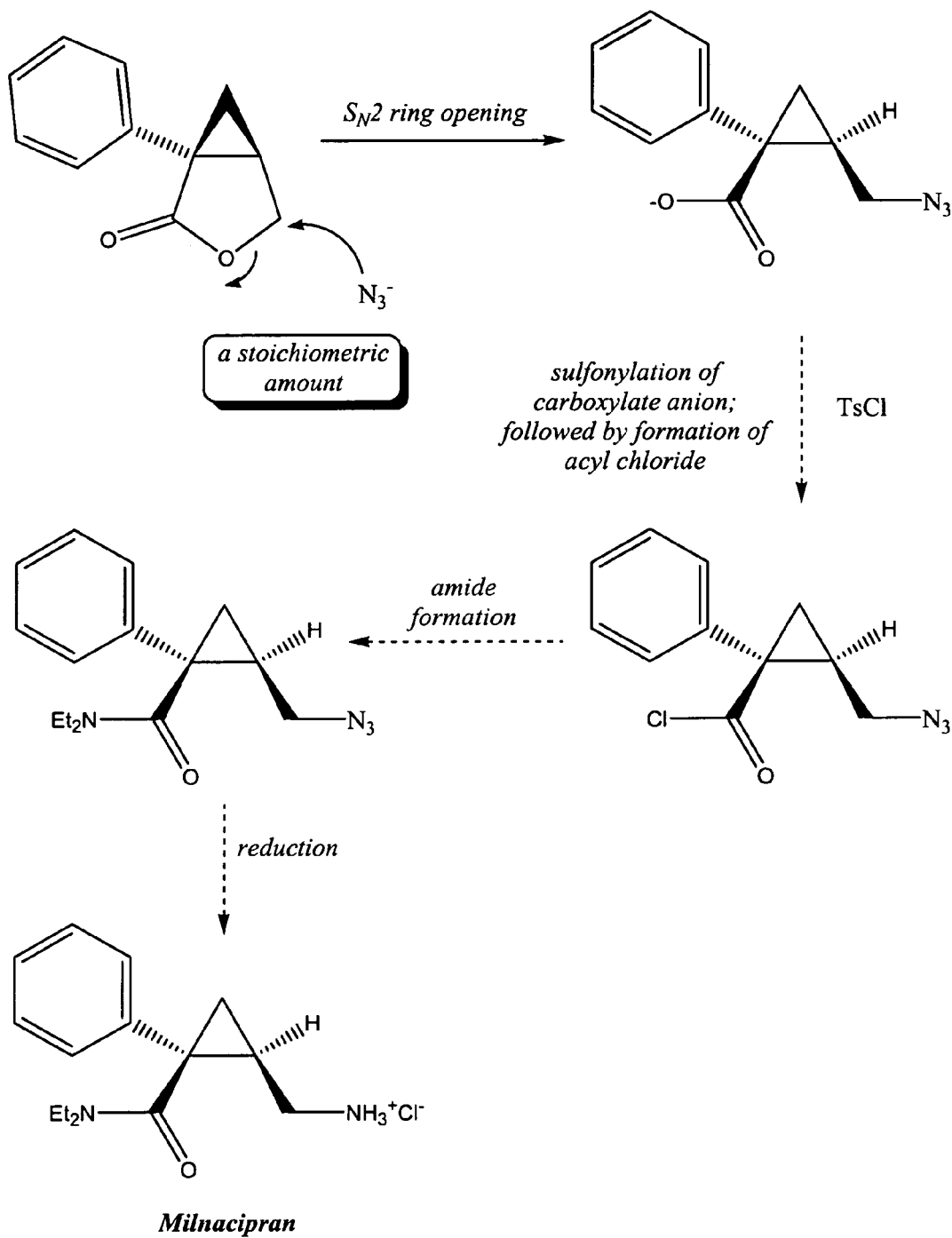
FIG. 10 depicts a preferred combination of the methods of the present invention, which taken together constitutes a scheme for the synthesis of milnacipran.
Figure 11:
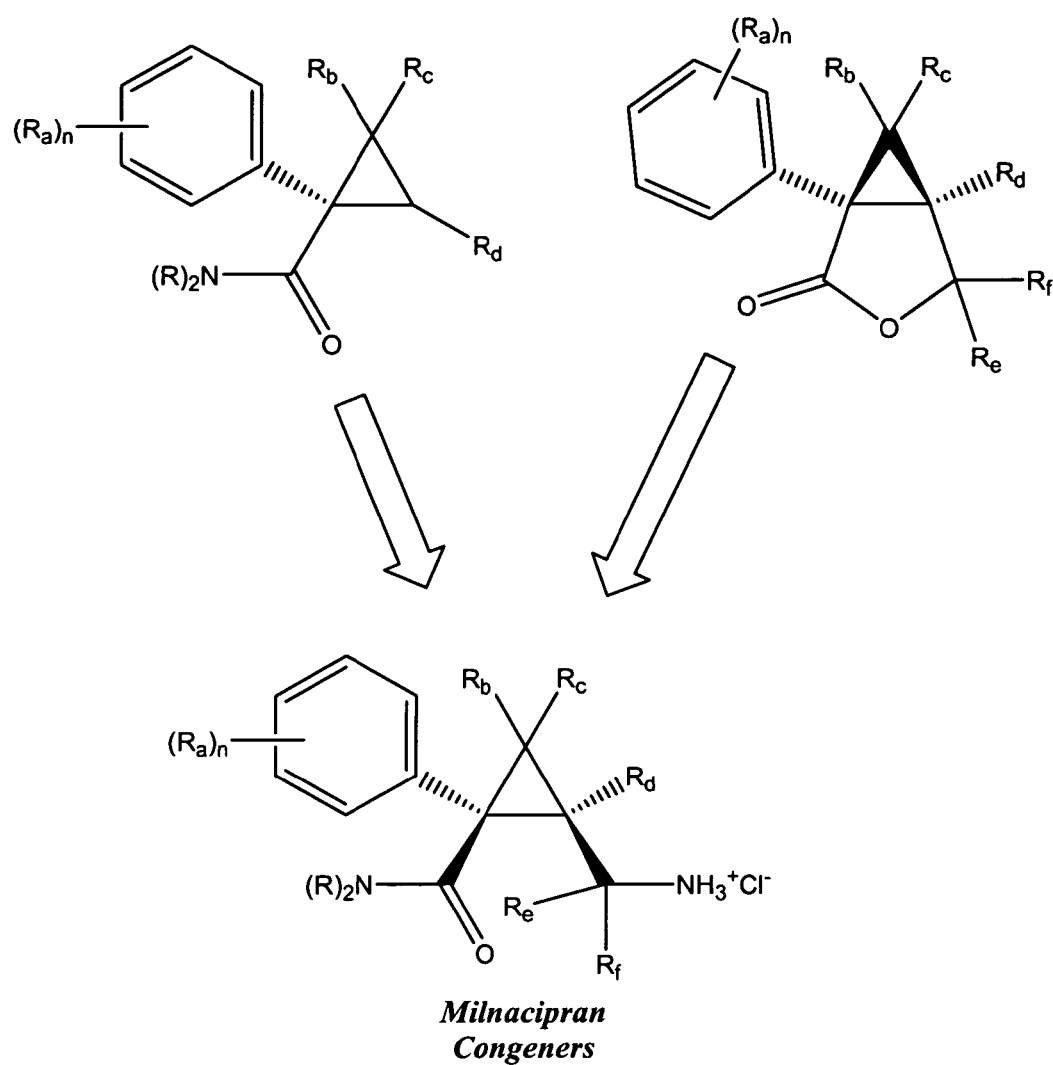
FIG. 11 depicts an overview of two preferred classes of starting materials for use in the methods of the present invention, which starting materials provide access to racemic and enantiomerically enriched milnacipran congeners.

The methods disclosed herein provide a variety of alternative routes for the synthesis of milnacipran and congeners thereof. See, e.g., FIGS. 1-11. For example, ring-opening of the optionally substituted 1-phenyl-2-oxo-3-oxa-bicyclo[3.1.0]hexane lactone (1) can occur either at the 1-position or the 2-position. See Scheme I. In a preferred embodiment, the lactone ring can be opened by attack of a nucleophile, either anionic or neutral, at the 2 position to generate a carboxylate ion (2).

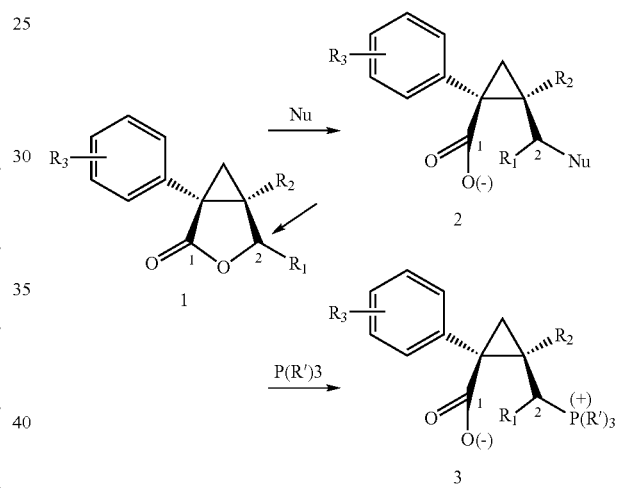

Scheme 1

When the nucleophile is an amine anion or otherwise possesses a nucleophilic nitrogen atom, the product of the reaction can be converted into compound 2, wherein R comprises the nitrogen atom required for milnacipran. For example, if the nucleophile is an azide ion or a phthalimide anion, the product will be compound 2, wherein R is $N_3$ or phthalimido, respectively. See Example 3 for an example when R is phtalimido.

Compound 1 will also react with a halide ion, e.g., iodide, to give the ring opened primary alkyl halide, i.e., compound 2, wherein R is halogen. Alternatively, compound 1 reacts with a phosphine to form phosphonium ion 3. Representative phosphines are tributylphosphine, triphenylphosphine, and other alkyl phosphines or aryl phosphines or alkylarylphosphines.

The aforementioned primary alkyl halides (2, wherein Nu is a halide) or compound 3 may likewise be converted into compound 2, wherein Nu comprises the nitrogen atom required for milnacipran. For example, the tributyl phosphonium ion (3, wherein R' is butyl) or primary iodide (2, wherein Nu is I) can be readily converted into compounds 2b and 2c by treatment with azide ion or phthalimide ion, respectively. See Scheme II.

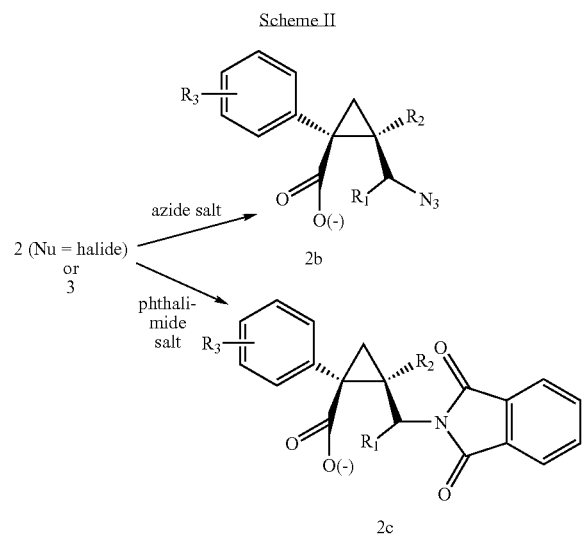

Treatment of azide 2b with tosyl chloride will provide acyl chloride 4. Compound 4 may then be readily converted into milnacipran or congeners thereof by treatment with an amine, such as diethylamine, followed by reduction of the azide moiety to the corresponding primary amine, and treatment with dilute aqueous hydrochloric acid. See Scheme III.

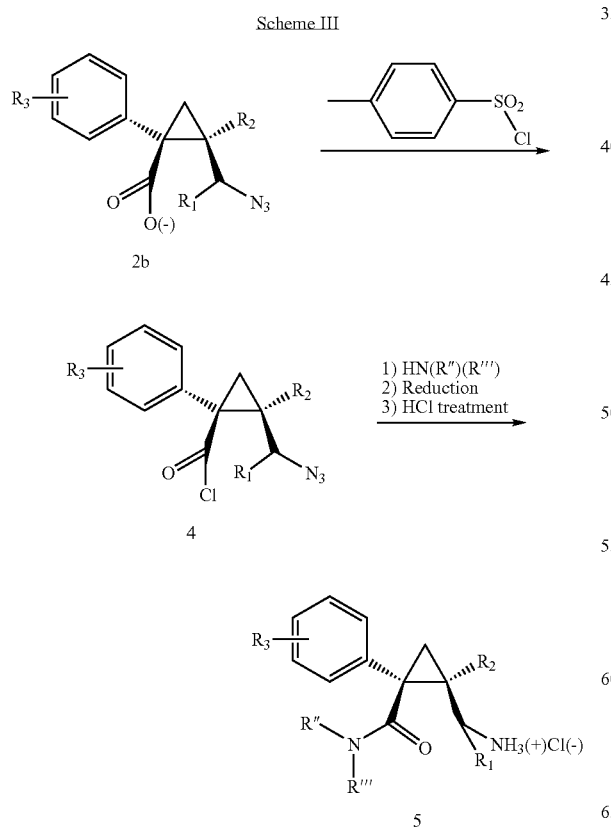

Phthalimide 2c can be converted into compound 5 by reaction under appropriate conditions, e.g., thionyl chloride or oxalyl chloride or a carbodiimide, of the carboxylate moiety with an amine, such as diethylamine, to give an amide (6). Removal of the protecting group, e.g., using hydrazine, followed by treatment with dilute aqueous hydrochloric acid will provide milnacipran or congeners thereof (5). See Scheme IV.

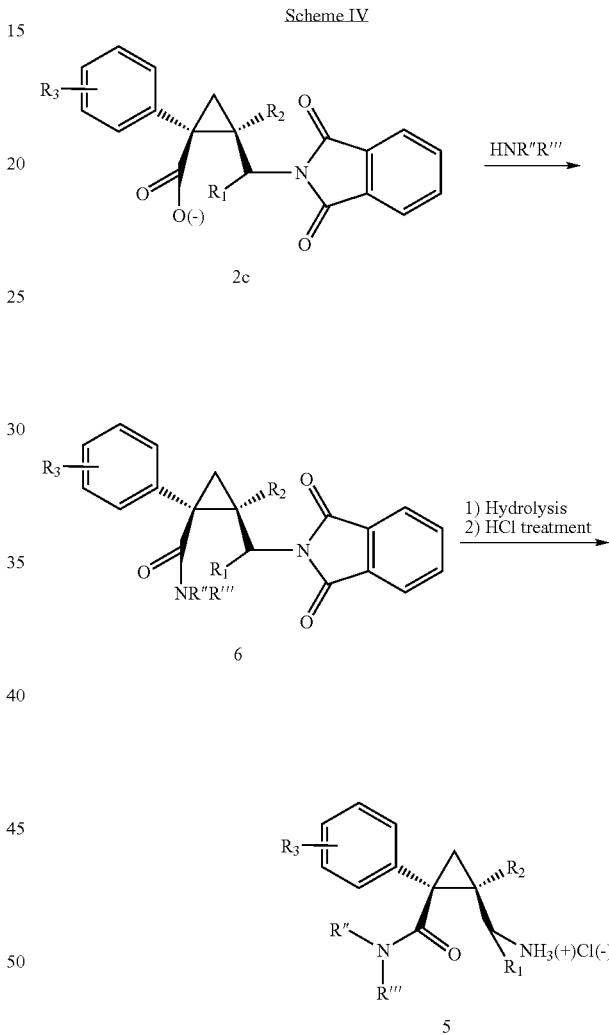

In another preferred embodiment, lactone 1 may be treated with lithium diethylamide to form compound 7 via chemoselective attack at the lactone's carbonyl moiety. Scheme V. Amide 7 may then be converted into a sulfonate 8 by treatment with a sulfonylating agent, e.g., mesyl chloride or tosyl azide. Sulfonate 8 may then be transformed into phthalimide 6 by reaction with a phthalimide salt, e.g., potassium phthalimide salt. Finally, compound 6 may be converted to milnacipran or congeners thereof (5) as outlined above.

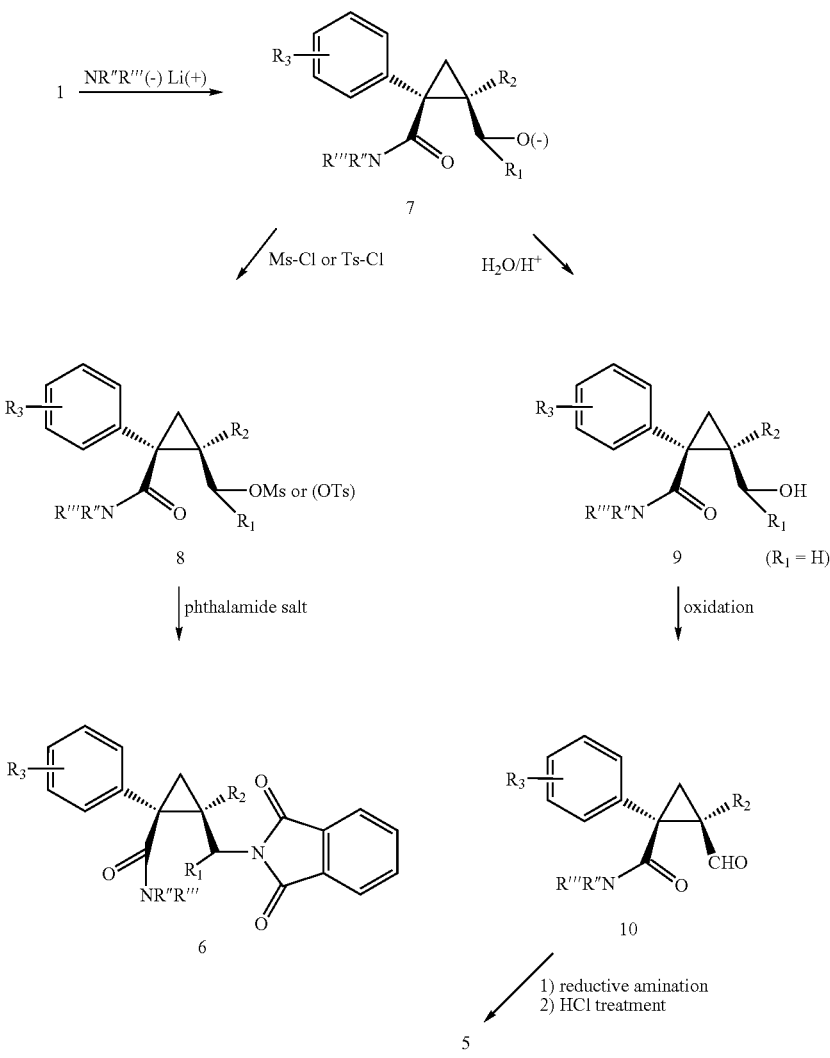

In another preferred embodiment, amide 7 may be oxidized to the corresponding aldehyde 10. See Scheme V. Aldehyde 10 may then be subjected to reductive amination, e.g., using sodium cyanoborohydride and ammonium acetate, followed by conversion to milnacipran or congeners thereof (5) as outlined above.

In a preferred embodiment, milnacipran and congeners thereof (5) may be synthesized in enantiomerically enriched form. See Scheme VI. This asymmetric embodiment of the methods of the present invention exploits the chiral-amine-based asymmetric lithiation methods. See, e.g., Beak, P. et al. *J. Am. Chem. Soc.* 1997, 119, 11561-11570; and Beak, P. et al. *J. Am. Chem. Soc.* 1997, 119, 8209-8216. Initially, 1,1-disubstituted cyclopropanes 12 are prepared from 2-arylacetamides 11. Then, asymmetric lithiation of the cyclopropane ring of 12 is achieved using the aforementioned methods; subsequently, the lithiated cyclopropane intermediate (not pictured) is quenched with a imine electrophile, e.g., $CH_2$=$NBn_2$ cation, to give compound 13, wherein the electrophile is cis to the amide moiety. Finally, compound 13 may be converted to milnacipran or congeners thereof (5) by hydrogenolytic removal of the benzyl groups followed by treatment with dilute aqueous hydrochloric acid.

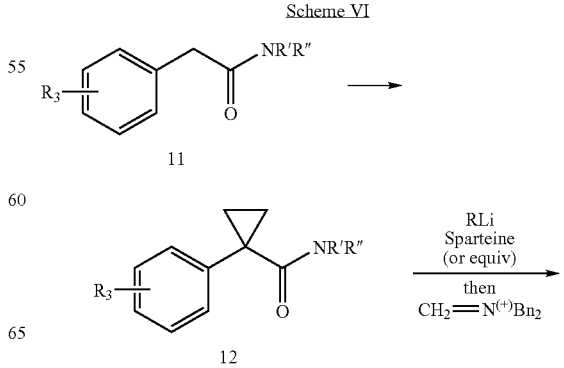

-continued

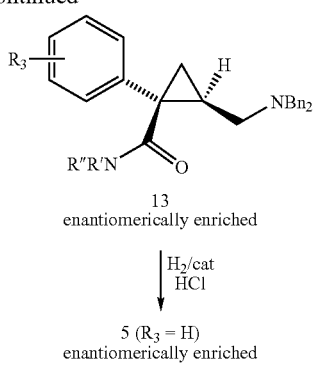

13
enantiomerically enriched

| H₂/cat
| HCl 5 (R₃ = H)
enantiomerically enriched

As noted above, the methods of the present invention are well suited to the preparation of congeners of milnacipran. For example, in certain embodiments, the present invention relates to the use of lactone 15 or cyclopropane 16 in the aforementioned methods to give a para-hydroxyl metabolite of milnacipran. See Scheme VII. Further, the present invention also relates to methods of preparing lactones 15 and cyclopropanes 16 from compounds 14.

Scheme VII

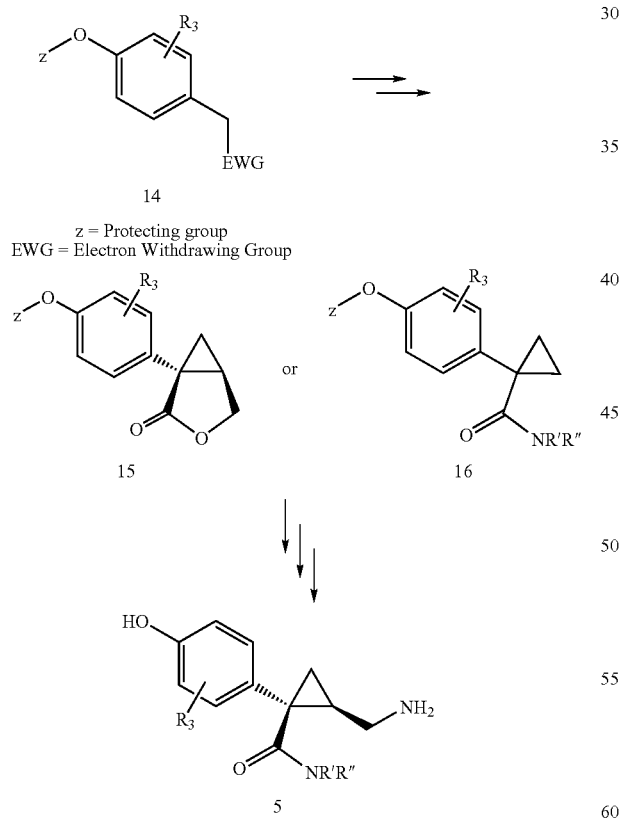

Treatment of lactone 1 with stoichiometric tosyl azide and a catalytic amount of azide will provide azide acyl sulfonate 17. Compound 17 may then be readily converted into milnacipran or congeners thereof by treatment with an amine, such as diethylamine, followed by reduction of the azide moiety to the corresponding primary amine, and treatment with dilute aqueous hydrochloric acid. See Scheme VIII.

Scheme VIII

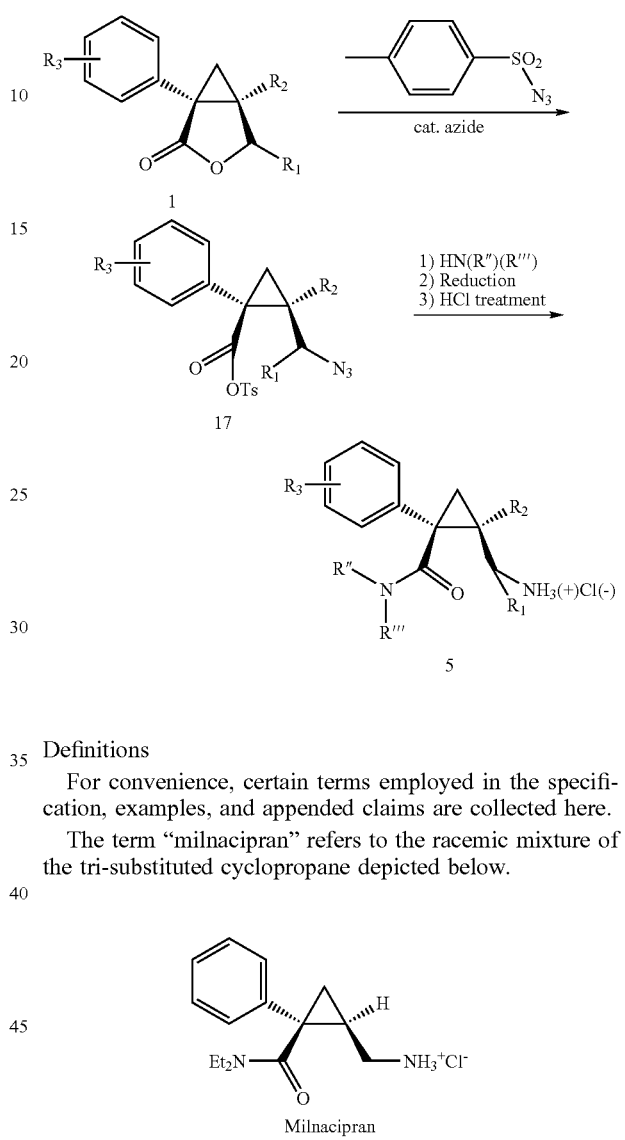

Definitions

For convenience, certain terms employed in the specification, examples, and appended claims are collected here.

The term "milnacipran" refers to the racemic mixture of the tri-substituted cyclopropane depicted below.

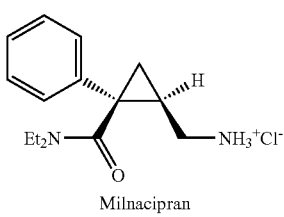

Milnacipran

As used herein, the term "LHMDS" means lithium hexamethyldisilazide; "KHMDS" means potassium hexamethyldisilazide; "LDA" means lithium diisopropyl amide; "BMDA" means bromomagnesium diisopropyl amide; "PSO" means phenylsulfonyl oxaziridine; "THF" means tetrahydrofuran; "mCPBA" means meta-chloroperbenzoic acid; "TES" means triethylsilyl; "TMS" means trimethylsilyl; "Tf" means —SO₂CF₃; "TEA" means triethylamine; "t-BuLi" means tert-butyllithium; "PDC" means pyridinium dichromate; "LAH" means lithium aluminum hydride; "TBHP" means tert-butyl hydroperoxide; "TTIP" means titanium tetraisoprepoxide; "protected hydroxy" means —OP, wherein P is a hydroxy protecting group; and "hydroxy protecting group" includes, but is not limited to, acetals having two to ten carbons, ketals having two to ten carbons, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoro-acetyl; and carbonates including but not limited to alkyl carbonates having from one to six carbon atoms, such as methyl, ethyl, n-propyl, isopropyl, n-butyl, t-butyl; isobutyl, and n-pentyl; alkyl carbonates having from one to six carbon atoms and substituted with one or more halogen atoms, such as 2,2,2-trichloroethoxymethyl and 2,2,2-trichloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Additional hydroxyl protecting groups may be found in "Protective Groups in Organic Synthesis" by T. W. Greene, John Wiley and Sons, 1981, and Second Edition, 1991.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, J. March, *Advanced Organic Chemistry*, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, alkylsulfonyl, arylsulfonyl, trifluoromethyl, cyano, chloride, and the like. Exemplary electron-donating groups include amino, methoxy, and the like.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings.

Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of *Advanced Inorganic Chemistry* by Cotton and Wilkinson.

The terms "amine" and "amino" are art-recognized and refer to both unsubstituted and substituted amines, e.g., a moiety that may be represented by the general formulas:

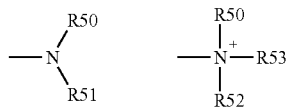

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

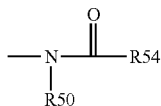

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

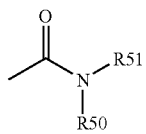

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

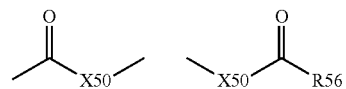

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

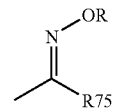

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

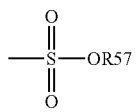

in which R57 is an electron pair, hydrogen, alkyl, cycloalkyl, or aryl.

The term "sulfate" is art recognized and includes a moiety that may be represented by the general formula:

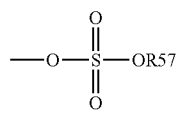

in which R57 is as defined above.

The term "sulfonamido" is art recognized and includes a moiety that may be represented by the general formula:

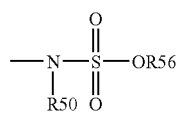

in which R50 and R56 are as defined above.

The term "sulfamoyl" is art-recognized and refers to a moiety that may be represented by the general formula:

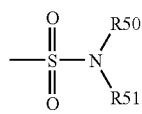

in which R50 and R51 are as defined above.

The term "sulfonyl" is art-recognized and refers to a moiety that may be represented by the general formula:

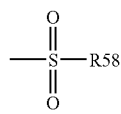

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

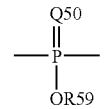

wherein Q50 represents S or O, and R59 represents hydrogen, a lower alkyl or an aryl. When used to substitute, e.g., an alkyl, the phosphoryl group of the phosphorylalkyl may be represented by the general formulas:

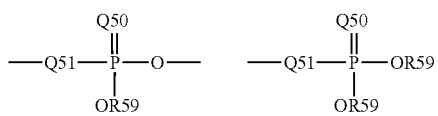

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

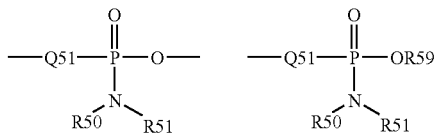

wherein Q51, R50, R51 and R59 are as defined above.

The term "phosphonamidite" is art-recognized and may be represented in the general formulas:

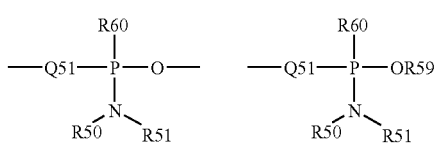

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

Methods of the Invention

In certain embodiments, the present invention relates to a method represented by Scheme A:

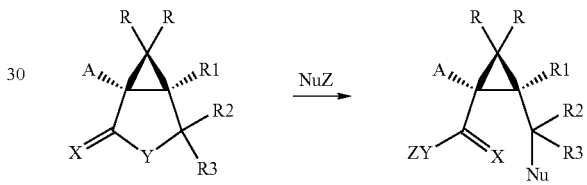

wherein

X represents O, S or NR';

Y represents O, S, or NR';

R' represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$;

Nu represents a compound, moiety, or anion comprising a nucleophilic atom selected from the group consisting of nitrogen, phosphorus, oxygen, chloride, bromide, and iodide; wherein said nucleophilic atom attacks the substrate forming a covalent bond and displacing Y;

Z represents a pair of electrons, H, alkali metal cation, alkaline earth cation, main-group metal cation, transition metal cation, ammonium cation, or sulfonium cation;

A represents optionally substituted aryl, heteroaryl, aralkyl or heteroaralkyl;

R represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$;

R1 represents H, alkyl, cycloalkyl, alkenyl, aryl, heteroaryl, arylalkyl, or —$(CH_2)_m$—$R_{80}$;

R2 represents H, alkyl, cycloalkyl, alkenyl, aryl, heteroaryl, arylalkyl, or —$(CH_2)_m$—$R_{80}$;

R3 represents H;

$R_{80}$ represents independently for each occurrence an aryl, cycloalkyl, cycloalkenyl, heterocyclyl, or polycyclyl moiety; and m is independently for each occurrence an integer in the range 0 to 8 inclusive.

In certain embodiments, the present invention relates to a method represented by Scheme A and the attendant definitions, wherein X represents O. In certain embodiments, the present invention relates to a method represented by Scheme A and the attendant definitions, wherein Y represents O. In certain embodiments, the present invention relates to a method represented by Scheme A and the attendant definitions, wherein A represents optionally substituted phenyl. In certain embodiments, the present invention relates to a method represented by Scheme A and the attendant definitions, wherein R represents H. In certain embodiments, the present invention relates to a method represented by Scheme A and the attendant definitions, wherein R1 represents H. In certain embodiments, the present invention relates to a method represented by Scheme A and the attendant definitions, wherein R2 represents H. In certain embodiments, the present invention relates to a method represented by Scheme A and the attendant definitions, wherein X represents O; and Y represents O. In certain embodiments, the present invention relates to a method represented by Scheme A and the attendant definitions, wherein X represents O; Y represents O; and A represents optionally substituted phenyl. In certain embodiments, the present invention relates to a method represented by Scheme A and the attendant definitions, wherein X represents O; Y represents O; A represents optionally substituted phenyl; and R represents H. In certain embodiments, the present invention relates to a method represented by Scheme A and the attendant definitions, wherein X represents O; Y represents O; A represents optionally substituted phenyl; R represents H; and R1 represents H. In certain embodiments, the present invention relates to a method represented by Scheme A and the attendant definitions, wherein X represents O; Y represents O; A represents optionally substituted phenyl; R represents H; R1 represents H; and R2 represents H.

In certain embodiments, the present invention relates to a method represented by Scheme A wherein X represents O, S or NR'; Y represents O, S, or NR'; R' represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, suffliydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$; Nu represents a compound, moiety, or anion comprising a nucleophilic nitrogen atom; wherein said nucleophilic nitrogen atom attacks the substrate forming a covalent bond and displacing Y; Z represents a pair of electrons, H, alkali metal cation, alkaline earth cation, main-group metal cation, transition metal cation, ammonium cation, or sulfonium cation; A represents optionally substituted aryl, heteroaryl, aralkyl or heteroaralkyl; R represents independently for each occurrence H, alkyl, cycloalkyl, alkenyl, aryl, heteroaryl, arylalkyl, cyano, halogen, hydroxyl, alkoxyl, aryloxy, arylakyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$; R1 represents H, alkyl, cycloalkyl, alkenyl, aryl, heteroaryl, arylalkyl, or —$(CH_2)_m$—$R_{80}$; R2 represents H, alkyl, cycloalkyl, alkenyl, aryl, heteroaryl, arylalkyl, or —$(CH_2)_m$—$R_{80}$; R3 represents H; $R_{80}$ represents independently for each occurrence an aryl, cycloalkyl, cycloalkenyl, heterocyclyl, or polycyclyl moiety; and m is independently for each occurrence an integer in the range 0 to 8 inclusive.

In certain embodiments, the present invention relates to a method represented by Scheme A and the attendant definitions, wherein X represents O; Y represents O; A represents optionally substituted phenyl; R represents H; R1 represents H; and R2 represents H.

In certain embodiments, the present invention relates to a method represented by Scheme A wherein X represents O, S or NR'; Y represents O, S, or NR'; R' represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$; NuZ represents

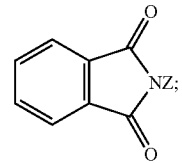

Z represents a pair of electrons, H, alkali metal cation, alkaline earth cation, main-group metal cation, transition metal cation, ammonium cation, or sulfonium cation; A represents optionally substituted aryl, heteroaryl, aralkyl or heteroaralkyl; R represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$; R1 represents H, alkyl, cycloalkyl, alkenyl, aryl, heteroaryl, arylalkyl, or —$(CH_2)_m$—$R_{80}$; R2 represents H, alkyl, cycloalkyl, alkenyl, aryl, heteroaryl, arylalkyl, or —$(CH_2)_m$—$R_{80}$; R3 represents H; $R_{80}$ represents independently for each occurrence an aryl, cycloalkyl, cycloalkenyl, heterocyclyl, or polycyclyl moiety; and m is independently for each occurrence an integer in the range 0 to 8 inclusive.

In certain embodiments, the present invention relates to a method represented by Scheme A and the attendant definitions, wherein Z represents an alkali metal cation. In certain embodiments, the present invention relates to a method represented by Scheme A and the attendant definitions, wherein Z represents K⁺. In certain embodiments, the present invention relates to a method represented by Scheme A and the attendant definitions, wherein X represents O; Y represents O; A represents optionally substituted phenyl; R represents H; R1 represents H; and R2 represents H. In certain embodiments, the present invention relates to a method represented by Scheme A and the attendant definitions, wherein X represents O; Y represents O; A represents optionally substituted phenyl; R represents H; R1 represents H; R2 represents H; and Z represents an alkali metal cation. In certain embodiments, the present invention relates to a method represented by Scheme A and the attendant definitions, wherein X represents O; Y represents O; A represents optionally substituted phenyl; R represents H; R1 represents H; R2 represents H; and Z represents $K^+$.

In certain embodiments, the present invention relates to a method represented by Scheme B:

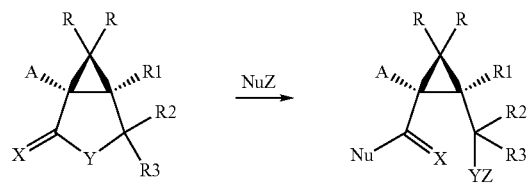

Scheme B wherein

X represents O, S or NR;

Y represents O, S, or NR;

Nu represents a compound, moiety, or anion comprising a nucleophilic atom selected from the group consisting of nitrogen, phosphorus, oxygen, chloride, bromide, and iodide; wherein said nucleophilic atom attacks the substrate forming a covalent bond and displacing Y; provided that when Nu is a dialkyl amide anion, the method does not comprise a Lewis acid;

Z represents a pair of electrons, H, alkali metal cation, alkaline earth cation, main-group metal cation, transition metal cation, ammonium cation, or sulfonium cation;

A represents optionally substituted aryl, heteroaryl, aralkyl or heteroaralkyl;

R represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$;

R1 represents H, alkyl, cycloalkyl, alkenyl, aryl, heteroaryl, arylalkyl, or —$(CH_2)_m$—$R_{80}$;

R2 represents H, alkyl, cycloalkyl, alkenyl, aryl, heteroaryl, arylalkyl, or —$(CH_2)_m$—$R_{80}$;

R3 represents H, alkyl, cycloalkyl, alkenyl, aryl, heteroaryl, arylalkyl, or —$(CH_2)_m$—$R_{80}$;

$R_{80}$ represents independently for each occurrence an aryl, cycloalkyl, cycloalkenyl, heterocyclyl, or polycyclyl moiety; and m is independently for each occurrence an integer in the range 0 to 8 inclusive.

In certain embodiments, the present invention relates to a method represented by Scheme B and the attendant definitions, wherein X represents O. In certain embodiments, the present invention relates to a method represented by Scheme B and the attendant definitions, wherein Y represents O. In certain embodiments, the present invention relates to a method represented by Scheme B and the attendant definitions, wherein A represents optionally substituted phenyl. In certain embodiments, the present invention relates to a method represented by Scheme B and the attendant definitions, wherein R represents H. In certain embodiments, the present invention relates to a method represented by Scheme B and the attendant definitions, wherein R1 represents H. In certain embodiments, the present invention relates to a method represented by Scheme B and the attendant definitions, wherein R2 represents H; and R3 represents H. In certain embodiments, the present invention relates to a method represented by Scheme B and the attendant definitions, wherein X represents O; and Y represents O. In certain embodiments, the present invention relates to a method represented by Scheme B and the attendant definitions, wherein X represents O; Y represents O; and A represents optionally substituted phenyl. In certain embodiments, the present invention relates to a method represented by Scheme B and the attendant definitions, wherein X represents O; Y represents O; A represents optionally substituted phenyl; and R represents H. In certain embodiments, the present invention relates to a method represented by Scheme B and the attendant definitions, wherein X represents O; Y represents O; A represents optionally substituted phenyl; R represents H; and R1 represents H. In certain embodiments, the present invention relates to a method represented by Scheme B and the attendant definitions, wherein X represents O; Y represents O; A represents optionally substituted phenyl; R represents H; R1 represents H; R2 represents H; and R3 represents H.

In certain embodiments, the present invention relates to a method represented by Scheme C:

Scheme C

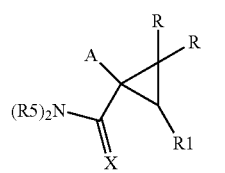

1) ZLi in combination with or followed by a non-racemic chiral tertiary amine; or conjugate base of a non-racemic chiral secondary amine
2) R2

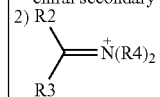

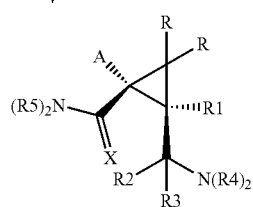

wherein

X represents O, S or NR;

Z represents alkyl, aryl or $N(R5)_2$;

tertiary amine represents a non-chiral or chiral teriary amine; wherein a chiral tertiary amine is a racemic mixture, enantiomerically enriched, or a single enantiomer;

A represents optionally substituted aryl, heteroaryl, aralkyl or heteroaralkyl;

R represents independently for each occurrence H, alkyl, cycloalkyl, alkenyl, aryl, heteroaryl, arylalkyl, or —(CH$_2$)$_m$—R$_{80}$;

R1 represents H, alkyl, cycloalkyl, alkenyl, aryl, heteroaryl, arylalkyl, or —(CH$_2$)$_m$—R$_{80}$;

R2 represents H, alkyl, cycloalkyl, alkenyl, aryl, heteroaryl, arylalkyl, or —(CH$_2$)$_m$—R$_{80}$;

R3 represents H, alkyl, cycloalkyl, alkenyl, aryl, heteroaryl, arylalkyl, or —(CH$_2$)$_m$—R$_{80}$;

R4 represents independently for each occurrence H, alkyl, cycloalkyl, alkenyl, aryl, heteroaryl, arylalkyl, or —(CH$_2$)$_m$—R$_{80}$;

R5 represents independently for each occurrence alkyl, cycloalkyl, alkenyl, aryl, heteroaryl, arylalkyl, or —(CH$_2$)$_m$—R$_{80}$;

R$_{80}$ represents independently for each occurrence an aryl, cycloalkyl, cycloalkenyl, heterocyclyl, or polycyclyl moiety;

m is independently for each occurrence an integer in the range 0 to 8 inclusive; and the product is a racemic mixture, enantiomerically enriched, or a single enantiomer.

In certain embodiments, the present invention relates to a method represented by Scheme C and the attendant definitions, wherein X represents O. In certain embodiments, the present invention relates to a method represented by Scheme C and the attendant definitions, wherein A represents optionally substituted phenyl. In certain embodiments, the present invention relates to a method represented by Scheme C and the attendant definitions, wherein R represents H. In certain embodiments, the present invention relates to a method represented by Scheme C and the attendant definitions, wherein R1 represents H. In certain embodiments, the present invention relates to a method represented by Scheme C and the attendant definitions, wherein R2 represents H. In certain embodiments, the present invention relates to a method represented by Scheme C and the attendant definitions, wherein R3 represents H. In certain embodiments, the present invention relates to a method represented by Scheme C and the attendant definitions, wherein R4 represents benzyl. In certain embodiments, the present invention relates to a method represented by Scheme C and the attendant definitions, wherein R5 represents ethyl. In certain embodiments, the present invention relates to a method represented by Scheme C and the attendant definitions, wherein X represents O; and A represents optionally substituted phenyl. In certain embodiments, the present invention relates to a method represented by Scheme C and the attendant definitions, wherein X represents O; A represents optionally substituted phenyl; and R represents H. In certain embodiments, the present invention relates to a method represented by Scheme C and the attendant definitions, wherein X represents O; A represents optionally substituted phenyl; R represents H; and R1 represents H. In certain embodiments, the present invention relates to a method represented by Scheme C and the attendant definitions, wherein X represents O; A represents optionally substituted phenyl; R represents H; R1 represents H; and R2 represents H. In certain embodiments, the present invention relates to a method represented by Scheme C and the attendant definitions, wherein X represents O; A represents optionally substituted phenyl; R represents H; R1 represents H; R2 represents H; and R3 represents H. In certain embodiments, the present invention relates to a method represented by Scheme C and the attendant definitions, wherein X represents O; A represents optionally substituted phenyl; R represents H; R1 represents H; R2 represents H; R3 represents H; and R4 represents benzyl. In certain embodiments, the present invention relates to a method represented by Scheme C and the attendant definitions, wherein X represents O; A represents optionally substituted phenyl; R represents H; R1 represents H; R2 represents H; R3 represents H; R4 represents benzyl; and R5 represents ethyl. In certain embodiments, the present invention relates to a method represented by Scheme C and the attendant definitions, wherein X represents O; A represents optionally substituted phenyl; R represents H; R1 represents H; R2 represents H; R3 represents H; R4 represents benzyl; R5 represents ethyl; and the product is enantiomerically enriched or a single enantiomer.

In certain embodiments, the present invention relates to a method represented by Scheme D:

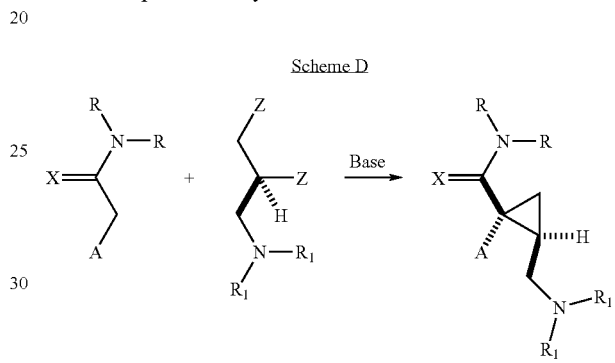

Scheme D wherein

X represents O, S or NR;

A represents optionally substituted aryl, heteroaryl, aralkyl or heteroaralkyl;

Z represents independently for each occurrence Cl, Br, I, OS(O)$_2$(aryl), OS(O)$_2$(alkyl), OS(O)$_2$O(aryl), OS(O)$_2$O(alkyl), acyloxy, OC(O)O(aryl), OC(O)O(alkyl), OC(O)NH(aryl), or OC(O)NH(alkyl); or the two instances of Z taken together represent OS(O)O or OS(O)$_2$O; base represents greater than or equal to about two equivalents of a Bronsted base;

R represents independently for each occurrence H, alkyl, cycloalkyl, alkenyl, aryl, heteroaryl, aralkyl, or —(CH$_2$)$_m$—R$_{80}$;

R1 represents independently for each occurrence H, alkyl, cycloalkyl, alkenyl, aryl, heteroaryl, aralkyl, formyl, acyl, alkylsulfonyl, arylsulfonyl, alkoxycarbonyl, alkenyloxycarbonyl, aryloxycarbonyl, tri(alkyl)silyl, tri(aryl)silyl or —(CH$_2$)$_m$—R$_{80}$;

R$_{80}$ represents independently for each occurrence an aryl, cycloalkyl, cycloalkenyl, heterocyclyl, or polycyclyl moiety;

m is independently for each occurrence an integer in the range 0 to 8 inclusive;

the reagent comprising two Z groups is enantiomerically enriched or enantiomerically pure; and the product is enantiomerically enriched or enantiomerically pure.

In certain embodiments, the present invention relates to a method represented by Scheme D and the attendant definitions, wherein X represents O. In certain embodiments, the present invention relates to a method represented by Scheme D and the attendant definitions, wherein A represents optionally substituted phenyl. In certain embodiments, the present invention relates to a method represented by Scheme D and the attendant definitions, wherein Z represents independently for each occurrence Br, I, OS(O)$_2$(aryl), OS(O)$_2$(alkyl), OS(O)$_2$O(aryl), OS(O)$_2$O(alkyl), OC(O)O(aryl) or OC(O)O(alkyl); or the two instances of Z taken together represent OS(O)O or OS(O)$_2$O. In certain embodiments, the present invention relates to a method represented by Scheme D and the attendant definitions, wherein R represents independently for each occurrence H or aralkyl. In certain embodiments, the present invention relates to a method represented by Scheme D and the attendant definitions, wherein R1 represents independently for each occurrence aralkyl. In certain embodiments, the present invention relates to a method represented by Scheme D and the attendant definitions, wherein X represents O; and A represents optionally substituted phenyl. In certain embodiments, the present invention relates to a method represented by Scheme D and the attendant definitions, wherein X represents O; A represents optionally substituted phenyl; and Z represents independently for each occurrence Br, I, OS(O)$_2$(aryl), OS(O)$_2$(alkyl), OS(O)$_2$O(aryl), OS(O)$_2$O(alkyl), OC(O)O(aryl) or OC(O)O(alkyl); or the two instances of Z taken together represent OS(O)O or OS(O)$_2$O. In certain embodiments, the present invention relates to a method represented by Scheme D and the attendant definitions, wherein X represents O; A represents optionally substituted phenyl; Z represents independently for each occurrence Br, I, OS(O)$_2$(aryl), OS(O)$_2$(alkyl), OS(O)$_2$O(aryl), OS(O)$_2$O(alkyl), OC(O)O(aryl) or OC(O)O(alkyl); or the two instances of Z taken together represent OS(O)O or OS(O)$_2$O; and R represents independently for each occurrence H or aralkyl. In certain embodiments, the present invention relates to a method represented by Scheme D and the attendant definitions, wherein X represents O; A represents optionally substituted phenyl; Z represents independently for each occurrence Br, I, OS(O)$_2$(aryl), OS(O)$_2$(alkyl), OS(O)$_2$O(aryl), OS(O)$_2$O(alkyl), OC(O)O(aryl) or OC(O)O(alkyl); or the two instances of Z taken together represent OS(O)O or OS(O)$_2$O; R represents independently for each occurrence H or aralkyl; and R$_1$ represents independently for each occurrence aralkyl. In certain embodiments, the present invention relates to a method represented by Scheme D and the attendant definitions, wherein X represents O; A represents optionally substituted phenyl; Z represents independently for each occurrence Br, I, OS(O)$_2$(aryl), OS(O)$_2$(alkyl), OS(O)$_2$O(aryl), OS(O)$_2$O(alkyl), OC(O)O(aryl) OC(O)O(alkyl); or the two instances of Z taken together represent OS(O)O or OS(O)$_2$O; R represents independently for each occurrence H or benzyl; and R$_1$ represents independently for each occurrence benzyl. In certain embodiments, the present invention relates to a method represented by Scheme D and the attendant definitions, wherein X represents O; A represents optionally substituted phenyl; Z represents independently for each occurrence OS(O)$_2$(aryl), or OS(O)$_2$(alkyl); or the two instances of Z taken together represent OS(O)$_2$O; R represents independently for each occurrence H or benzyl; and R$_1$ represents independently for each occurrence benzyl.

In certain embodiments, the present invention relates to a method represented by Scheme E:

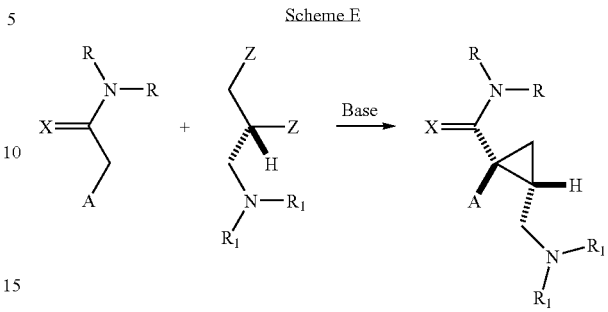

Scheme E wherein
X represents O, S or NR;
Z represents independently for each occurrence Cl, Br, I, OS(O)$_2$(aryl), OS(O)$_2$(alkyl), OS(O)$_2$O(aryl), OS(O)$_2$O(alkyl), acyloxy, OC(O)O(aryl), OC(O)O(alkyl), OC(O)NH(aryl), or OC(O)NH(alkyl); or the two instances of Z taken together represent OS(O)O or OS(O)$_2$O;
A represents optionally substituted aryl, heteroaryl, aralkyl or heteroaralkyl; base represents greater than or equal to about two equivalents of a Bronsted base;
R represents independently for each occurrence H, alkyl, cycloalkyl, alkenyl, aryl, heteroaryl, aralkyl, or —(CH$_2$)$_m$—R$_{80}$;
R$_1$ represents independently for each occurrence H, alkyl, cycloalkyl, alkenyl, aryl, heteroaryl, aralkyl, formyl, acyl, alkylsulfonyl, arylsulfonyl, alkoxycarbonyl, alkenyloxycarbonyl, aryloxycarbonyl, tri(alkyl)silyl, tri(aryl)silyl or —(CH$_2$)$_m$—R$_{80}$;
R$_{80}$ represents independently for each occurrence an aryl, cycloalkyl, cycloalkenyl, heterocyclyl, or polycyclyl moiety;
m is independently for each occurrence an integer in the range 0 to 8 inclusive;
the reagent comprising two Z groups is enantiomerically enriched or enantiomerically pure; and
the product is enantiomerically enriched or enantiomerically pure.

In certain embodiments, the present invention relates to a method represented by Scheme E and the attendant definitions, wherein X represents O. In certain embodiments, the present invention relates to a method represented by Scheme E and the attendant definitions, wherein A represents optionally substituted phenyl. In certain embodiments, the present invention relates to a method represented by Scheme E and the attendant definitions, wherein Z represents independently for each occurrence Br, I, OS(O)$_2$(aryl), OS(O)$_2$(alkyl), OS(O)$_2$O(aryl), OS(O)$_2$O(alkyl), OC(O)O(aryl) or OC(O)O(alkyl); or the two instances of Z taken together represent OS(O)O or OS(O)$_2$O. In certain embodiments, the present invention relates to a method represented by Scheme E and the attendant definitions, wherein R represents independently for each occurrence H or aralkyl. In certain embodiments, the present invention relates to a method represented by Scheme E and the attendant definitions, wherein R$_1$ represents independently for each occurrence aralkyl. In certain embodiments, the present invention relates to a method represented by Scheme E and the attendant definitions, wherein X represents O; and A represents optionally substituted phenyl. In certain embodiments, the present invention relates to a method represented by Scheme E and the attendant definitions, wherein X represents O; A represents optionally substituted phenyl; and Z represents independently for each occurrence Br, I, $OS(O)_2$(aryl), $OS(O)_2$(alkyl), $OS(O)_2O$(aryl), $OS(O)_2O$(alkyl), $OC(O)O$(aryl) or $OC(O)O$(alkyl); or the two instances of Z taken together represent $OS(O)O$ or $OS(O)_2O$. In certain embodiments, the present invention relates to a method represented by Scheme E and the attendant definitions, wherein X represents O; A represents optionally substituted phenyl; Z represents independently for each occurrence Br, I, $OS(O)_2$(aryl), $OS(O)_2$(alkyl), $OS(O)_2O$(aryl), $OS(O)_2O$(alkyl), $OC(O)O$(aryl) or $OC(O)O$(alkyl); or the two instances of Z taken together represent $OS(O)O$ or $OS(O)_2O$; and R represents independently for each occurrence H or aralkyl. In certain embodiments, the present invention relates to a method represented by Scheme E and the attendant definitions, wherein X represents O; A represents optionally substituted phenyl; Z represents independently for each occurrence Br, I, $OS(O)_2$(aryl), $OS(O)_2$(alkyl), $OS(O)_2O$(aryl), $OS(O)_2O$(alkyl), $OC(O)O$(aryl) or $OC(O)O$(alkyl); or the two instances of Z taken together represent $OS(O)O$ or $OS(O)_2O$; R represents independently for each occurrence H or aralkyl; and $R_1$ represents independently for each occurrence aralkyl. In certain embodiments, the present invention relates to a method represented by Scheme E and the attendant definitions, wherein X represents O; A represents optionally substituted phenyl; Z represents independently for each occurrence Br, I, $OS(O)_2$(aryl), $OS(O)_2$(alkyl), $OS(O)_2O$(aryl), $OS(O)_2O$(alkyl), $OC(O)O$(aryl) or $OC(O)O$(alkyl); or the two instances of Z taken together represent $OS(O)O$ or $OS(O)_2O$; R represents independently for each occurrence H or benzyl; and $R_1$ represents independently for each occurrence benzyl. In certain embodiments, the present invention relates to a method represented by Scheme E and the attendant definitions, wherein X represents O; A represents optionally substituted phenyl; Z represents independently for each occurrence $OS(O)_2$(aryl), or $OS(O)_2$(alkyl); or the two instances of Z taken together represent $OS(O)_2O$; R represents independently for each occurrence H or benzyl; and $R_1$ represents independently for each occurrence benzyl.

Subsequent Transformations

A product synthesized by a method of the present invention may be either an end-product or an intermediate in a synthesis scheme. In cases where the product synthesized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, analgesics, and antidepressants.

Reaction Conditions

The methods of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants or the product. For example, the reaction temperature influences the speed of the reaction, as well as the stability of the reactants, products and catalyst.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofliran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures. Furthermore, one or more of the reactants or the catalyst can be immobilized by attachment to or incorporation into a polymer or other insoluble matrix.

Suitable Acids

A wide range of Bronsted and Lewis acids are suitable for use in the methods of the present invention. In general, where a method requires the use of Bronsted acid, i.e., a proton donor, any mono-, di- or tri-protic acid may be used. In certain embodiments, a method of the present invention will use a Bronsted acid selected from the group consisting of hydrogen chloride gas, aqueous hydrochloric acid solutions, phosphoric acid, sulfuric acid, nitric acid, p-toluenesulfonic acid, and mixtures thereof.

A variety of Lewis acids, i.e., electron-pair acceptors, are useful in the methods of the present invention. Main-group metal halides, such as $AlCl_3$ and $BF_3$, may be used in the methods of the present invention. Transition metal halides, e.g., $TiCl_4$ and $SnCl_4$, are also useful in the methods of the present invention. Lewis acids useful in the methods of the present invention also include organic metallic compounds of rare earth metals of scandium (Sc), yttrium (Y), and lanthanide (Ln) series, for example, trifluoromethanesulfonates of rare earth metals, such as scandium trifluoromethanesulfonate (scandium triflate), yttrium triflate, and lanthanide triflates (Ln=La, Ce, Pr, Nd, Sm, Eu, Gd, Th, Dy, Ho, Er, Tm, Yb, and Lu).

Moreover, metallocene compounds may be used as Lewis acids in the methods of the present invention. In certain embodiments, a suitable metallocene is selected from the group consisting of pentamethylcyclopentadienyltitanium isopropoxide, pentamethylcyclopentadienyltribenzyl titanium, dimethylsilyltetramethyl-cyclopentadienyl-tert-butylamido titanium dichloride, pentamethylcyclopentadienyl titanium trimethyl, dimethylsilyltetramethylcyclopentadienyl-tert-butylamido zirconium dimethyl, dimethylsilyltetramethylcyclopentadienyl-dodecylamido hafnium dihydride, dimethylsilyltetramethylcyclopentadienyl-dodecylamido hafnium dimethyl, unbridged biscyclopentadienyl compounds such as bis(1,3-butyl, methylcyclopentadienyl) zirconium dimethyl, pentamethylcyclopentadienyl-cyclopentadienyl zirconium dimethyl, (tetramethylcyclopentadienyl)(n-propylcyclopetadienyl)zirconium dimethyl; bridged bis-cyclopentadienyl compounds such as dimethylsilylbis (tetrahydroindenyl) zirconium dichloride and silacyclobutyl (tetramethylcyclopentadienyl)(n-propyl-cyclopentadienyl) zirconium dimethyl; bridged bisindenyl compounds such as dimethylsilylbisindenyl zirconium dichloride, dimethylsilylbisindenyl hafnium dimethyl, dimethylsilylbis(2-methyl-benzindenyl) zirconium dichloride, dimethylsilylbis(2-methylbenzindenyl) zirconium dimethyl; and fluorenyl ligand-containing compounds, e.g., diphenylmethyl(fluorenyl) (cyclopentadienyl)zirconiumdimethyl.

Suitable Bases

Likewise, a wide range of Bronsted and Lewis bases are suitable for use in the methods of the present invention. The base may optionally be sterically hindered to discourage coordination of the base.

Exemplary bases include such as, by way of example only: alkoxides such as sodium tert-butoxide; alkali metal amides such as sodium amide, lithium diisopropylamide, and alkali metal bis(trialkylsilyl)amide, e.g., such as lithium bis(trimethylsilyl)amide (LiHMDS) or sodium bis(trimethylsilyl)amide (NaHMS); tertiary amines (e.g. triethylamine, trimethylamine, 4-(dimethylamino)pyridine (DMAP), 1,5-diazabicycl[4.3.0]non-5-ene (DBN), 1,5-diazabicyclo[5.4.0] undec-5-ene (DBU); alkali or alkaline earth carbonate, bicarbonate or hydroxide (e.g. sodium, magnesium, calcium, barium, potassium carbonate, phosphate, hydroxide and bicarbonate). By way of example only, suitable bases include NaH, LiH, KH, $K_2CO_3$, $Na_2CO_3$, $Tl_2CO_3$, $Cs_2CO_3$, K(OtBu), Li(OtBu), Na(OtBu) K(OAr), Na(OAr), and triethylamine, or mixtures thereof. Preferred bases include CsF, $K_3PO_4$, DBU, NaOt-Bu, KOt-Bu, $LiN(i-Pr)_2$ (LDA), $KN(SiMe_3)_2$, $NaN(SiMe_3)_2$, and $LiN(SiMe_3)_2$.

In certain embodiments, a method of the present invention will use an amine as a Bronsted base, e.g., a tertiary amine, such as trialkylamines having 1 to 4 carbon atoms in the alkyl, such as trimethyl- and triethylamine, and trialkanolamines having 2 or 3 carbon atoms in the alkanol residue, preferably triethanolamine, tri-n-propanolamine or triisopropanolamine.

In certain embodiments, a Lewis base suitable for use in the methods of the present invention is selected from the group consisting of:

(i) esters, such as methyl formate, ethyl formate, butyl formate, isobutyl formnate, pentyl formate, methyl acetate, ethyl acetate, propyl acetate, isopropyl acetate, butyl acetate, isobutyl acetate, pentyl acetate, isopentyl acetate, hexyl acetate, cyclohexyl acetate, benzyl acetate, 3-methoxybutyl acetate, 2-ethylbutyl acetate, 3-ethylhexylacetate, 3-methoxybutyl acetate, methyl propionate, ethyl propionate, butyl propionate, isopentyl propionate, methyl butyrate, ethyl butyrate, butyl butyrate, isopentyl butyrate, isobutyl isobutyrate, ethyl isovalerate, isobutyl isovalerate, butyl stearate, pentyl stearate, methyl benzoate, ethyl benzoate, propyl benzoate, butyl benzoate, isopentyl benzoate, benzyl benzoate, ethyl cinnamate, diethyl oxalate, dibutyl oxalate, dipentyl oxalate, diethyl malonate, dimethyl maleate, diethyl maleate, dibutyl maleate, dimethyl phthalate, diethyl phthalate, dibutyl phthalate, diisobutyl phthalate, and triacetin;

(ii) amines, such as methylamine, dimethylamine, trimethylamine, ethylamine, diethylamine, triethylamine, propylamine, diisopropylamine, butylamine, isobutylamine, dibutylamine, tributylamine, pentylamine, dipentylamine, tripentylamine, 2-ethylhexylamine, allylamine, aniline, N-methylaniline, N,N-dimethylaniline, N,N-diethylaniline, toluidine, cyclohexylamine, dicyclohexylamine, pyrrole, piperidine, pyridine, picoline, 2,4-lutidine, 2,6-lutidine, 2,6-di(t-butyl) pyridine, quinoline, and isoquinoline;

(iii) ethers, such as diethyl ether, dipropyl ether, diisopropyl ether, dibutyl ether, dihexyl ether, anisole, phenetole, butyl phenyl ether, methoxytoluene, benzyl ethyl ether, diphenyl ether, dibenzyl ether, veratrole, 2-epoxypropane, dioxane, trioxane, furan, 2,5-dimethylfuran, tetrahydrofuran, tetrahydropyrane, 1,2-diethoxyethane, 1,2-dibutoxyethane, and crown ethers;

(iv) ketones, such as acetone, methyl ethyl ketone, methy propyl ketone, diethyl ketone, butyl methyl ketone, methyl isobutyl ketone, methyl pentyl ketone, dipropyl ketone, diisobutyl ketone, cyclohexanone, methylcyclohexanone, and acetophenone;

(v) thioethers, such as dimethyl sulfide, diethyl sulfide, thiophene, and tetrahydrothiophene;

(vi) silyl ethers, such as tetramethoxysilane, tetraethoxysilane, tetra(n-propoxy)silane, tetra(isopropoxy)silane, tetra(n-butoxy)silane, tetra(isopentoxy)silane, tetra(n-hexoxy)silane, tetraphenoxysilane, tetrakis(2-ethylhexoxy)silane, tetrakis(2-ethylbutoxy)silane, tetrakis(2-methoxyethoxy) silane, methyltrimethoxysilane, ethyltrimethoxysilane, n-propyltrimethoxysilane, isopropyltrimethoxysilane, n-butyltrimethoxysilane, isobutyltrimethoxysilane, sec-butyltrimethoxysilane, t-butyltrimethoxysilane, phenyltrimethoxysilane, vinyltrimethoxysilane, norbomyltrimethoxysilane, cyclohexyltrimethoxysilane, chloromethyltrimethoxysilane, 3-chloropropyltrimethoxysilane, chlorotrimethoxysilane, triethoxysilane, methyltriethoxysilane, ethyltriethoxysilane, n-propyltriethoxysilane, n-butyltriethoxysilane, phenyltriethoxysilane, vinyltriethoxysilane, 3-aminopropyltriethoxysilane, ethyltri(isopropoxy)silane, isopentyl(n-butoxy)silane, methyl(tri-n-hexoxy)silane, methyldimethoxysilane, diemthyldimethoxysilane, n-propylmethyldimethoxysilane, n-propylethyldimethoxysilane, di(n-propyl)dimethoxysilane, isopropylmethyldimethoxysilane, di(isopropyl)dimethoxysilane, n-propylisopropyldimethoxysilane, n-butylmethyldimethoxysilane, n-butylethyldimethoxysilane, n-butyl-n-propyldimethoxysilane, n-butylisopropyldimethoxysilane, di(n-butyl) dimethoxysilane, isobutylmethyldimethoxysilane, diisobutyldimethoxysilane, sec-butylethyldimethoxysilane, di(sec-butyl)dimethoxysilane, t-butylmethyldimethoxysilane, t-butyl-n-propyldimethoxysilane, di(t-butyl)dimethoxysilane, t-butyl-n-hexyldimethoxysilane, diisoamyldimethoxysilane, n-hexyl-n-propyldimethoxysilane, n-decylmethyldimethoxysilane, norbomylmethyldimethoxysilane, cyclohexylmethyldimethoxysilane, methylphenyldimethoxysilane, diphenyldimethoxysilane, dicyclopentyldimethoxysilne, dimethyldiethoxysilane, diethyldiethoxysilane, di(isopropyl)diethoxysilane, sec-butylmethyldiethoxysilane, t-butylmethyldiethoxysilane, dimethyl(n-butoxy)silane, trimethylmethoxysilane, trimethylethoxysilane, trimethylisopropoxysilane, trimethyl-n-propoxysilane, trimethyl-t-butoxysilane, trimethylisobutoxysilane, trimethyl-n-butoxysilane, trimethyl-n-pentoxysilane, and trimethylphenoxysilane;

(vii) phosphines, such as methylphosphine, ethylphosphine, phenylphosphine, benzylphosphine, dimethylphosphine, diethylphosphine, diphenylphosphine, methylphenylphosphine, trimethylphosphine, triethylphosphine, triphenylphosphine, tri(n-butyl) phosphine, ethylbenzylphenylphosphine, ethylbenzylbutylphosphine, trimethoxyphosphine, and diethylethoxyphosphine;

(viii) phosphine oxides, such as triphenylphosphie oxide, dimethylethoxyphosphie oxide, and triethoxyphosphine oxide;

(ix) nitriles, such as acrylonitrile, cyclohexanedintirile, and benzonitrile;

(x) nitro compounds, such as nitrobenzene, nitrotoluene, and dinitrobenzene;

(xi) acetals, such as acetone dimethylacetal, acetophenone dimethylacetal, benzophenone dimethylacetal, and cyclohexanone dimethylacetal;

(xii) carbonate esters, such as diethyl carbonate, diphenyl carbonate, and ethylene carbonate;

(xiii) thioacetals, such as 1-ethoxy-1-(methylthio)cyclopentane; and (xiv) thioketones such as cyclohexanethione.

Selected Uses of Compounds Prepared According to the Methods of the Present Invention There are numerous well established clinical uses of milnacipran. See, e.g., *Background of the Invention*; *The Merck Index*, 12$^{th}$ edition; Merck Research Laboratories Division, Merck & Co., Inc.; Whitehouse Station, N.J., USA; 1996; and *Physicians Desk Reference*, 53$^{rd}$ edition; Thomson Healthcare; Montvale, N.J., USA; 1999.

As discussed below in detail, compounds prepared according to the methods of the present invention may be formulated with a pharmaceutically acceptable excipient. Such a formulation may further comprise a compound selected from the group consisting of analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, and anti-narcoleptics. Alternatively, a formulation may comprise a compound selected from the group consisting of aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil, molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

Compounds prepared according to the methods of the invention are indicated for use in the treatment of depression, fibromyalgia syndrome, chronic fatigue syndrome, pain, attention deficit/hyperactivity disorder, visceral pain syndromes (VPS), irritable bowel syndrome (IBS), noncardiac chest pain (NCCP), functional dyspepsia, interstitial cystitis, essential vulvodynia, urethral syndrome, orchialgia, affective disorders, depressive disorders, major depressive disorder, dysthymia, atypical depression, anxiety disorders, generalized anxiety disorder, phobias, obsessive compulsive disorder, panic disorder, post-traumatic stress disorder, premenstrual dysphoric disorder, temperomandibular disorder, atypical face pain, migraine headache, or tension headache.

Fibromyalgia syndrome is a chronic and debilitating condition characterized by widespread pain and stiffness throughout the body, accompanied by severe fatigue and headache. It affects an estimated 2%-4% of the population worldwide and is the second most common diagnosis by rheumatologists in the United States, after osteoarthritis. Despite the high prevalence and severity of this syndrome, there are no approved treatments specifically for FMS in the United States or elsewhere. Compounds prepared according to the methods of the present invention may be used to treat fibromyalgia by adminstering a therapeutically effective amount of such a compound to a mammal in need thereof.

Pharmaceutical Compositions

In another aspect, the present invention relates to pharmaceutically acceptable compositions, comprising a therapeutically-effective amount of a compound made according to a method of the present invention; and a pharmaceutically acceptable carrier (additive) and/or diluent. As described in detail below, the pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated and/or solvated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with a compound selected from the group consisting of analgesics, anti-inflammatory drugs, antipyretics, antidepressants, anti-epileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, and anti-narcoleptics. Alternatively, a formulation may comprise a compound selected from the group consisting of aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil, molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof. Conjunctive therapy, thus includes sequential, simultaneous and separate administration of the active compound in a way that the therapeutical effects of the first administered one is not entirely disappeared when the subsequent is administered.

Combinatorial Libraries

The methods of the present invention readily lend themselves to being practiced via the methods of combinatorial chemistry, providing access to combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lemer et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly d etermine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B. Multipin Synthesis

The libraries of the subject method can take the multipin library format. Briefly, Geysen and co-workers (Geysen et al. (1984) PNAS 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811-5814; Valerio et al. (1991) Anal Biochem 197:168-177; Bray et al. (1991) Tetrahedron Lett 32:6163-6166).

C. Divide-Couple-Recombine

In yet another embodiment, a variegated library of compounds can be provided on a set of beads utilizing the strategy of divide-couple-recombine (see, e.g., Houghten (1985) PNAS 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D. Combinatorial Libraries by Light-Directed, Spatially Addressable Parallel Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271-280; Fodor, S. P. A. (1991) Science 251:767; Pirrung et al. (1992) U.S. Pat. No. 5,143,854; Jacobs et al. (1994) Trends Biotechnol 12:19-26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E. Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1. Tagging with sequenceable bio-oligomers: The principle of using oligonucleotides to encode combinatorial synthetic libraries was described in 1992 (Brenner et al. (1992) PNAS 89:5381-5383), and an example of such a library appeared the following year (Needles et al. (1993) PNAS 90:10700-10704). A combinatorial library of nominally $7^7$ (=823,543) peptides composed of all combinations of Arg, Gln, Phe, Lys, Val, d-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected NH2 groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529-2531), orthogonality in synthesis is achieved by employing acid-labile protection for the coding strand and base-labile protection for the compound strand.

In an alternative approach (Nikolaiev et al. (1993) Pept Res 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2. Non-sequenceable Tagging: Binary Encoding: An alternative form of encoding the test compound library employs a set of non-sequencable electrophoric tagging molecules that are used as a binary code (Ohlmeyer et al. (1993) PNAS 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode 240 (e.g., upwards of 1012) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

EXAMPLE 1

Synthesis of Compound 18

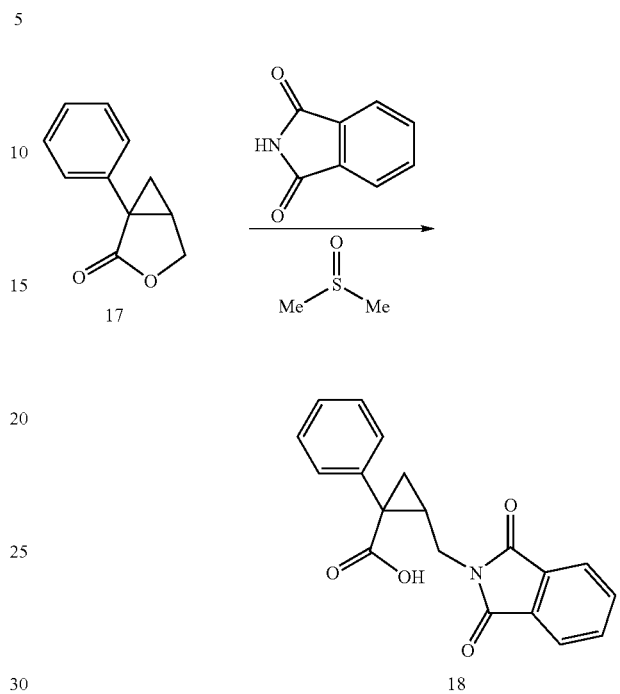

Figure 12:
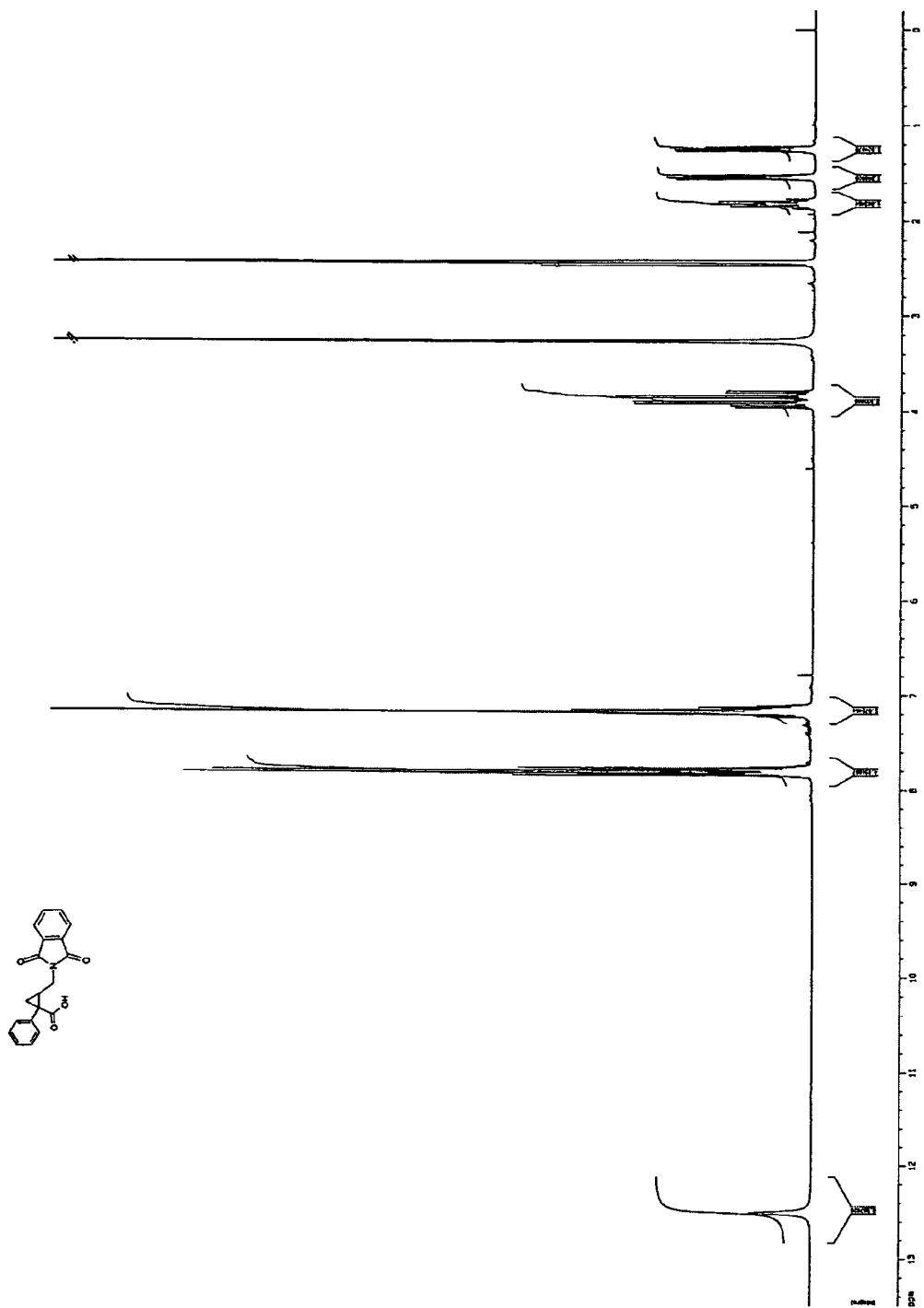
FIG. 12 depicts a $^1$H NMR spectrum of compound 18.
Figure 13:
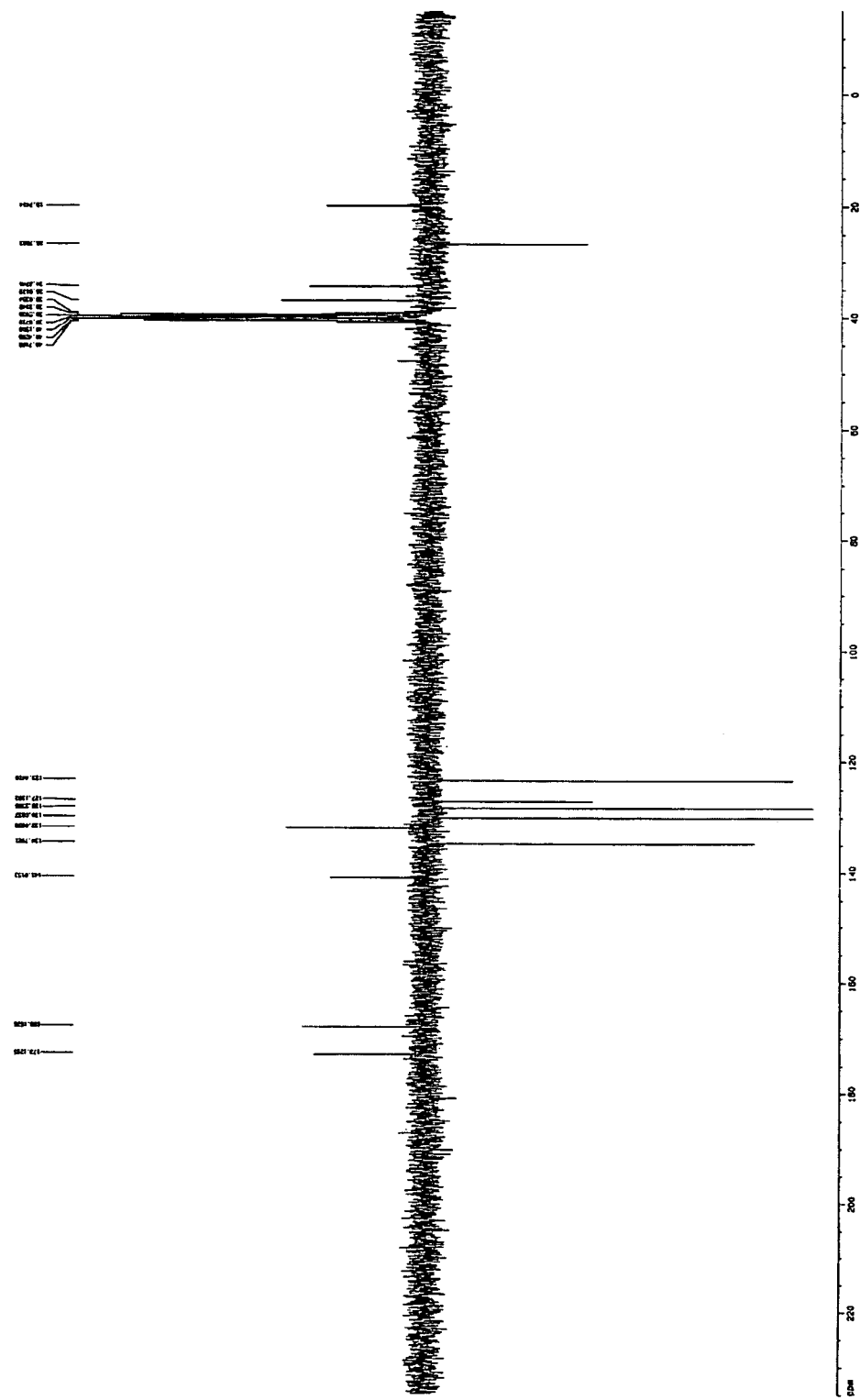
FIG. 13 depicts an APT $^{13}$C NMR spectrum of compound 18.
Figure 14:
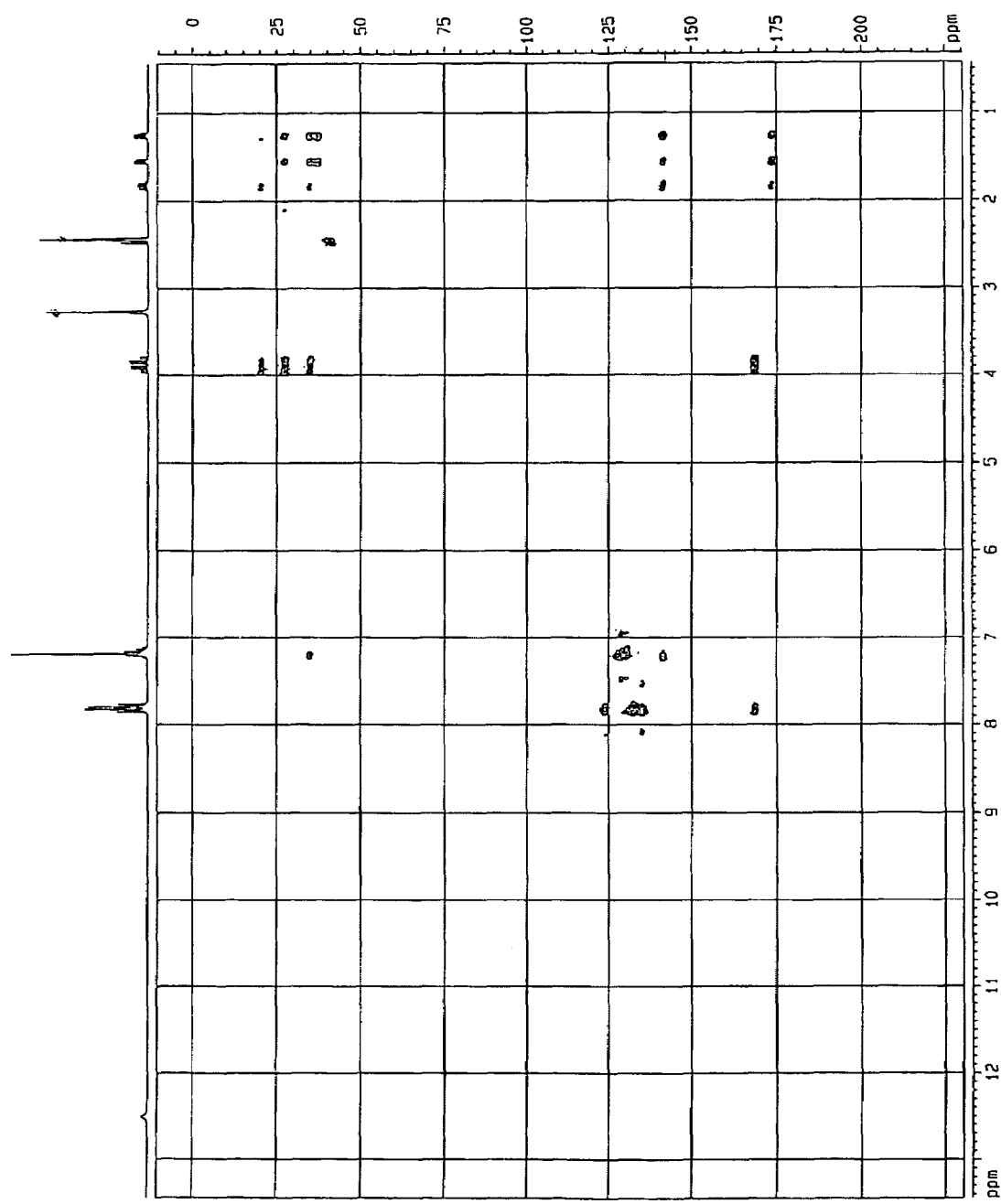
FIG. 14 depicts a HMBC $^{13}$C NMR spectrum of compound 18.
Figure 15:
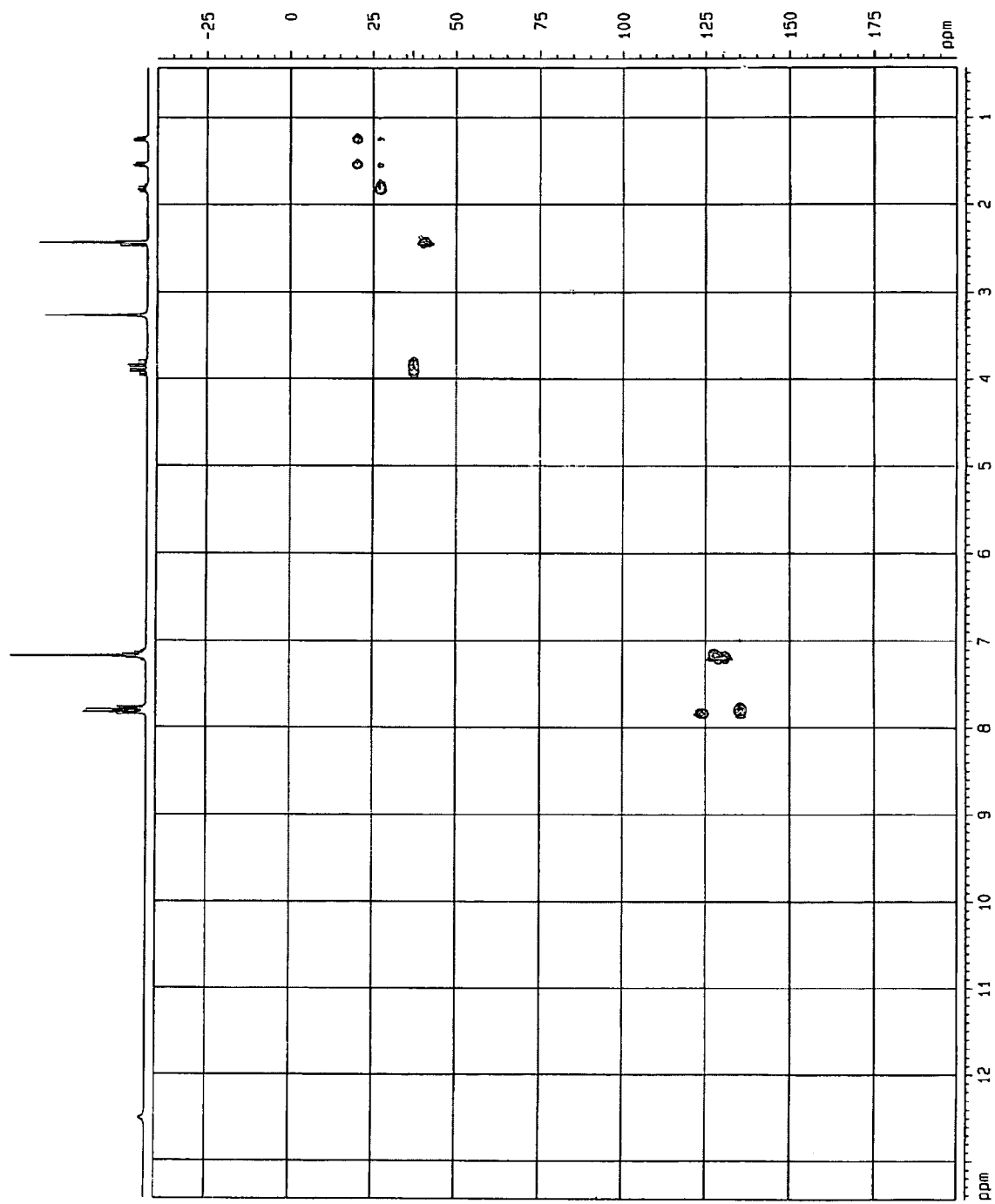
FIG. 15 depicts a HSQC $^{13}$C NMR spectrum of compound 18.

A 100 mL round bottom flask, equipped with a stir bar, a condensor and a gas adapter was charged with lactone 17 (870 mg, 5 mmol) and dry dimethyl sulphoxide (30 mL). The solution was stirred at ambient temperature followed by the addition of potassium phthalimide (952 mg, 5 mmol). The reaction mixture was heated using external heating (oil bath: 150° C.) for 20 h. Less than 5% of starting lactone 17 could be detected at this time. The mixture was poured on ice water (200 mL). The resulting mixture was adjusted to pH=5-6 by the addition of acetic acid. A precipitate formed. The mixture was filtered and the solid washed with cold water. After drying in vacuum (24 h, 50° C.) 18 (810 mg, 51%, LC purity: >95%) was obtained as a greyish solid. $^1$H NMR and $^{13}$C NMR (apt; hmbc; hsqc) are shown in FIGS. 12-15.

Note that lactone 17 was synthesized on a 0.54 mol scale according to a published method (J. Org. Chem. 1996, 61, 915-923). After filtration on silica, eluting with hexanes/ethyl acetate (2:1), lactone 17 (52 g, 55%) was obtained as a yellowish oil. The NMR and HPLC purities were above 98%.

EXAMPLE 2

Alternative Synthesis of Compound 18

The direct reaction of lactone 17 with potassium phthalimide is possible in polor protic solvents other than DMSO (Example 1), as shown below in Table 1 (entries 1-3). In addition, it mined that adding an iodine source (e.g. 10% TBAI) did not alter the lactone 17 LC % is percent conversion as measured by liquid chromatography.

TABLE 1

Reaction Conditions and Results

| entry | 17 [mmol] | phthalimide [mmol] | additive | solvent [mL] | temp. [° C.] | time [h] | 18 [LC %] |
|---|---|---|---|---|---|---|---|
| 1 | 10 | 10 | — | DMF [20] | 50-130 | 24 | 70 |
| 2 | 5 | 5 | — | NMP [30] | 150 | 20 | >90 |
| 3 | 5 | 5 | — | DMF [30] | 150 | 20 | >90 |
| 4 | 5 | 5 | 10% TBAI | NMP [30] | 150 | 20 | >90 |

Overall it was observed that the reaction is faster at higher temperatures (e.g., greater than about 100° C., preferably between about 120° C. and about 150° C.) and for optimal conversion the amount of solvent used should be large enough to ensure a homogenous solution (e.g. preferably a concentration between about 0.15 M and 0.50 M).

Additional Patents and Publications Cited

1. U.S. Pat. No. 4,478,836.
2. U.S. Pat. No. 5,034,541.
3. U.S. Pat. No. 5,621,142.
4. Moret, C. et al. *Neuropharmacology* 1985, 24, 1211-1219.
5. Bonnaud, B. et al. *J. Med. Chem.* 1987, 30, 318-325.
6. Shuto, S. et al. *J. Med. Chem.* 1995, 38, 2964-2968.
7. Viazzo, P. et al. *Tetrahedron Lett.* 1996, 37, 4519-4522.
8. Shuto, S. et al. *Tetrahedron Lett.* 1996, 37, 641-644.
9. Shuto, S. et al. *J. Med. Chem.* 1996, 39, 4844-4852.
10. Beak, P. et al. *J. Am. Chem. Soc.* 1997, 119, 8209-8216.
11. Beak, P. et al. *J. Am. Chem. Soc.* 1997, 119, 11561-11570.
12. Shuto, S. et al. *J. Med. Chem.* 1998, 41, 3507-3514.
13. Deprez, D. et al. *Eur. J. Drug Metab. Pharmacokinet.* 1998, 23, 166-171.
14. Puozzo, C. et al. *Eur. J. Drug Metab. Pharmacokinet.* 1998, 23, 273-279.
15. Puozzo C. et al. *Eur. J. Drug Metab. Pharmacokinet.* 1998, 23, 280-286.
16. Grard, S. et al. *Electrophoresis* 2000, 21, 3028-3034.
17. Shuto, S. et al. *Jpn. J. Pharmacol.* 2001, 85, 207-213.
18. Doyle, M. P. et al. *Adv. Synth. Catal.* 2001, 343, 299-302.
19. Kazuta, Y. et al. *Bioorg. Med. Chem.* 2002, 10, 1777-1791.
20. Labat, L. et al. *J. Chromatogr. B* 2002, 773, 17-23.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method represented by Scheme A:

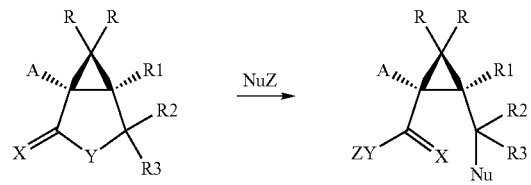

wherein

X represents O, S or NR';

Y represents O, S, or NR';

R' represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —(CH$_2$)$_m$—R$_{80}$;

NuZ represents

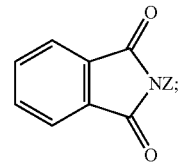

wherein the nitrogen atom of NuZ attacks the carbon atom of —Y—C(R2)(R3)— in the substrate, displacing Y and forming Nu—C(R2)(R3)— in the product;

Z represents a pair of electrons, H, alkali metal cation, alkaline earth cation, main-group metal cation, transition metal cation, ammonium cation, or sulfonium cation;

A represents optionally substituted aryl, heteroaryl, aralkyl or heteroaralkyl;

R represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —(CH$_2$)$_m$—R$_{80}$;

R1 represents H, alkyl, cycloalkyl, alkenyl, aryl, heteroaryl, arylalkyl, or —(CH$_2$)$_m$R$_{80}$;

R2 represents H, alkyl, cycloalkyl, alkenyl, aryl, heteroaryl, arylalkyl, or —(CH$_2$)$_m$R$_{80}$;

R3 represents H;

R$_{80}$ represents independently for each occurrence an aryl, cycloalkyl, cycloalkenyl, heterocyclyl, or polycyclyl moiety; and m is independently for each occurrence an integer in the range 0 to 8 inclusive.

2. The method of claim 1, wherein Z represents an alkali metal cation.

3. The method of claim 1, wherein Z represents $K^+$.

4. The method of claim 1, wherein X represents O; Y represents O; A represents optionally substituted phenyl; R represents H; R1 represents H; and R2 represents H.

5. The method of claim 1, wherein X represents O; Y represents O; A represents optionally substituted phenyl; R represents H; R1 represents H; R2 represents H; and Z represents an alkali metal cation.

6. The method of claim 1, wherein X represents O; Y represents O; A represents optionally substituted phenyl; R represents H; R1 represents H; R2 represents H; and Z represents $K^+$.

* * * * *